(12) United States Patent
Schafer et al.

(10) Patent No.: US 11,992,246 B2
(45) Date of Patent: *May 28, 2024

(54) SURGICAL BAND CLAMP SYSTEM

(71) Applicant: NuVasive, Inc., San Diego, CA (US)

(72) Inventors: Andrew Schafer, Encinitas, CA (US);
Andrew Morris, San Diego, CA (US);
Adam Lipson, San Diego, CA (US);
Robert German, San Diego, CA (US);
Nicholas Didier, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 554 days.

This patent is subject to a terminal disclaimer.

(21) Appl. No.: 17/140,898

(22) Filed: Jan. 4, 2021

(65) Prior Publication Data

US 2021/0186573 A1 Jun. 24, 2021

Related U.S. Application Data

(63) Continuation of application No. 16/391,724, filed on Apr. 23, 2019, now Pat. No. 10,945,770, which is a continuation of application No. 15/368,279, filed on Dec. 2, 2016, now Pat. No. 10,307,186.

(51) Int. Cl.
*A61B 17/70* (2006.01)
*A61B 17/88* (2006.01)

(52) U.S. Cl.
CPC ...... *A61B 17/7053* (2013.01); *A61B 17/8869* (2013.01)

(58) Field of Classification Search
CPC .......................... A61B 17/7053; A61B 17/8869

USPC .......................... 606/263, 86 A, 140
See application file for complete search history.

(56) References Cited

U.S. PATENT DOCUMENTS

| | | |
|---|---|---|
| 5,304,178 A | 4/1994 | Stahurski |
| 5,312,410 A | 5/1994 | Miller et al. |
| 5,395,374 A | 3/1995 | Miller et al. |
| 5,403,314 A | 4/1995 | Currier |
| 5,454,812 A | 10/1995 | Lin |
| 5,782,831 A | 7/1998 | Sherman et al. |
| 5,935,133 A | 8/1999 | Wagner et al. |
| 6,086,590 A | 7/2000 | Margulies et al. |
| 6,099,527 A | 8/2000 | Hochschuler et al. |
| 6,277,120 B1 | 8/2001 | Lawson |
| 6,514,255 B1 | 2/2003 | Ferree |
| 6,689,140 B2 | 2/2004 | Cohen |
| 6,695,852 B2 | 2/2004 | Gleason |
| 7,094,240 B2 | 8/2006 | Molz, IV et al. |
| 7,556,630 B2 | 7/2009 | Molz, IV et al. |
| 7,959,654 B2 | 6/2011 | Mazda et al. |
| 8,128,635 B2 | 3/2012 | Belliard et al. |
| 8,162,946 B2 | 4/2012 | Baccelli et al. |
| 8,172,843 B2 | 5/2012 | Baccelli et al. |
| 8,216,245 B2 | 7/2012 | Gil et al. |

(Continued)

FOREIGN PATENT DOCUMENTS

| | | |
|---|---|---|
| WO | 2009013397 A1 | 1/2009 |
| WO | 2013150445 A1 | 10/2013 |

*Primary Examiner* — Eduardo C Robert
*Assistant Examiner* — David C Comstock

(57) ABSTRACT

A system for securing a spinal rod to a bone structure using a connector is provided. The connector functions by modulating friction on a band in two band channels and locking the spinal rod in a separate rod channel. An instrument is also provided for tensioning the band.

20 Claims, 17 Drawing Sheets

(56) References Cited

U.S. PATENT DOCUMENTS

| | | | |
|---|---|---|---|
| 8,323,318 B2 | 12/2012 | Baccelli et al. | |
| 8,323,319 B2 | 12/2012 | Mazda et al. | |
| 8,430,918 B2 | 4/2013 | Baccelli et al. | |
| 8,465,495 B2 | 6/2013 | Belliard | |
| 8,465,527 B2 | 6/2013 | Clement | |
| 8,636,770 B2 | 1/2014 | Hestad et al. | |
| 8,721,645 B2 | 5/2014 | Belliard | |
| 8,728,083 B2 | 5/2014 | Baccelli et al. | |
| 8,747,405 B2 | 6/2014 | Belliard | |
| 8,801,759 B2 | 8/2014 | Mazda et al. | |
| 8,814,910 B2 | 8/2014 | Baccelli et al. | |
| 8,870,870 B2 | 10/2014 | Baccelli et al. | |
| 8,870,881 B2 | 10/2014 | Rezach et al. | |
| 9,039,708 B2 | 5/2015 | Larroque-Lahitette | |
| 9,039,711 B2 | 5/2015 | Mickiewicz et al. | |
| 9,084,644 B2 | 7/2015 | Knueppel | |
| 9,084,645 B2 | 7/2015 | Knueppel | |
| 9,101,406 B2 | 8/2015 | Belliard | |
| 9,113,963 B2 | 8/2015 | Baccelli et al. | |
| 9,113,966 B2 | 8/2015 | Baccelli et al. | |
| 9,173,685 B2 | 11/2015 | Lindquist et al. | |
| 9,204,902 B2 | 12/2015 | Belliard et al. | |
| 9,204,903 B2 | 12/2015 | Belliard et al. | |
| 9,370,390 B2 | 6/2016 | Mickiewicz et al. | |
| 9,393,051 B2 | 7/2016 | Baccelli et al. | |
| 9,675,386 B2 * | 6/2017 | Akbarnia | A61B 17/8869 |
| 10,945,770 B2 * | 3/2021 | Schafer | A61B 17/8869 |
| 2002/0040222 A1 | 4/2002 | Hashimoto et al. | |
| 2002/0072753 A1 | 6/2002 | Cohen | |
| 2004/0138666 A1 | 7/2004 | Molz, IV et al. | |
| 2005/0228375 A1 | 10/2005 | Mazda et al. | |
| 2008/0262551 A1 | 10/2008 | Rice et al. | |
| 2009/0105715 A1 | 4/2009 | Belliard et al. | |
| 2009/0138048 A1 | 5/2009 | Baccelli et al. | |
| 2009/0248077 A1 | 10/2009 | Johns | |
| 2009/0292317 A1 | 11/2009 | Belliard | |
| 2009/0326585 A1 | 12/2009 | Baccelli et al. | |
| 2010/0121387 A1 | 5/2010 | Belliard | |
| 2010/0249845 A1 | 9/2010 | Meunier et al. | |
| 2011/0112581 A1 | 5/2011 | Clement | |
| 2011/0166604 A1 | 7/2011 | Darst Rice et al. | |
| 2011/0238118 A1 | 9/2011 | Baccelli et al. | |
| 2011/0238125 A1 | 9/2011 | Baccelli et al. | |
| 2011/0245875 A1 | 10/2011 | Karim | |
| 2012/0022592 A1 | 1/2012 | Belliard | |
| 2012/0143207 A1 | 6/2012 | Belliard et al. | |
| 2012/0303121 A1 | 11/2012 | Douget et al. | |
| 2013/0261668 A1 | 10/2013 | Douget et al. | |
| 2013/0261680 A1 | 10/2013 | Baccelli et al. | |
| 2013/0325070 A1 | 12/2013 | Larroque-Lahitette et al. | |
| 2014/0066987 A1 | 3/2014 | Hestad et al. | |
| 2014/0094850 A1 | 4/2014 | Clement et al. | |
| 2014/0257397 A1 | 9/2014 | Akbarnia et al. | |
| 2014/0257400 A1 | 9/2014 | George et al. | |
| 2014/0257401 A1 | 9/2014 | George et al. | |
| 2014/0277149 A1 | 9/2014 | Rooney et al. | |
| 2014/0277207 A1 | 9/2014 | Baccelli et al. | |
| 2015/0351817 A1 | 12/2015 | Lindquist et al. | |
| 2016/0038194 A1 | 2/2016 | Belliard et al. | |
| 2016/0113682 A1 | 4/2016 | Altarac et al. | |
| 2016/0175014 A1 | 6/2016 | Albert et al. | |
| 2016/0242825 A1 | 8/2016 | Simpson et al. | |
| 2016/0249957 A1 | 9/2016 | Deneuvillers | |
| 2016/0262806 A1 | 9/2016 | Hsu et al. | |
| 2017/0172633 A1 | 6/2017 | Simpson | |
| 2017/0354445 A1 | 12/2017 | Deneuvillers et al. | |
| 2018/0029824 A1 | 2/2018 | Gephart et al. | |
| 2018/0098799 A1 | 4/2018 | Songer | |
| 2018/0289404 A1 | 10/2018 | Shoshtaev | |
| 2018/0296251 A1 * | 10/2018 | Palmer | A61B 17/7041 |

* cited by examiner

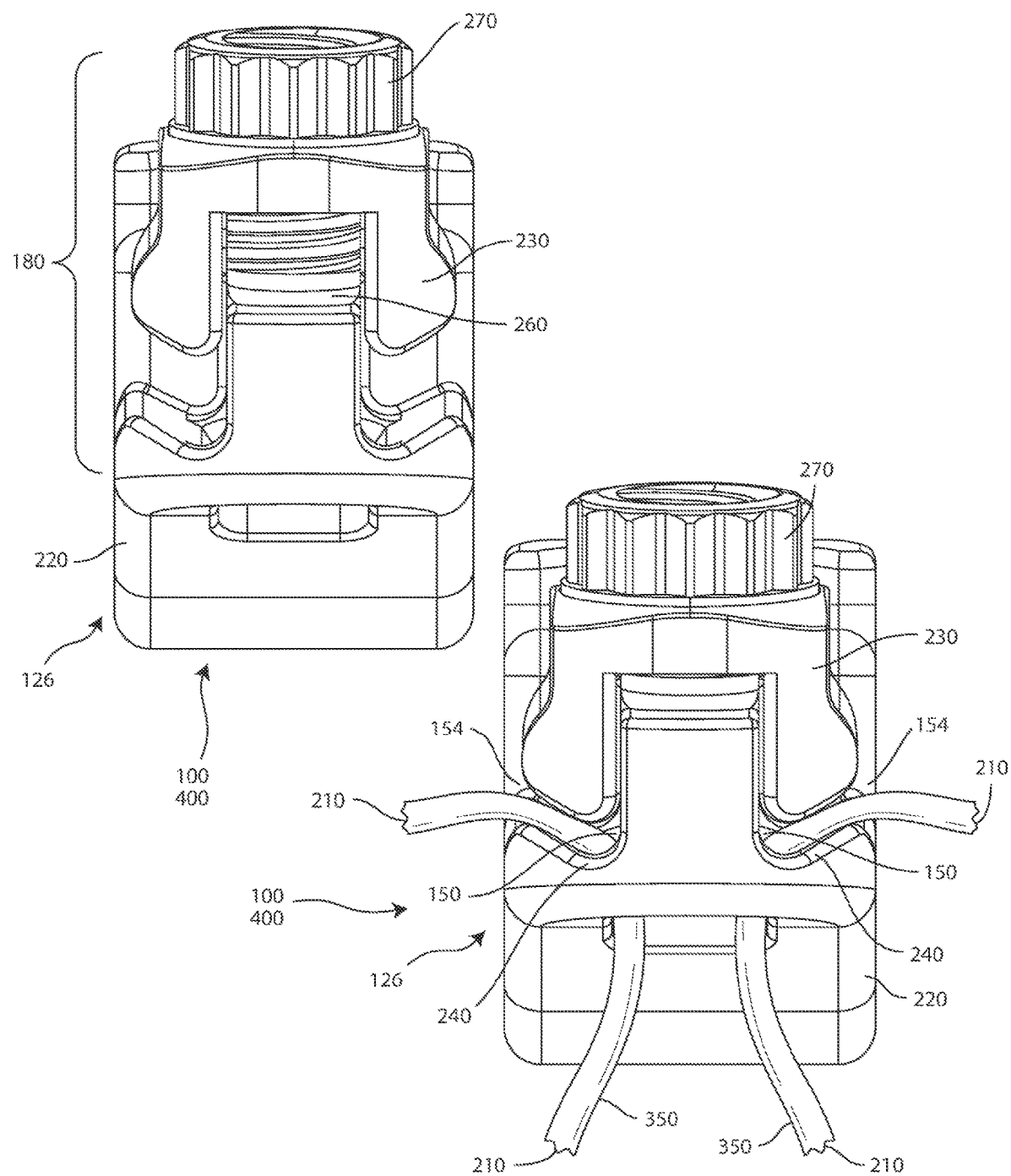

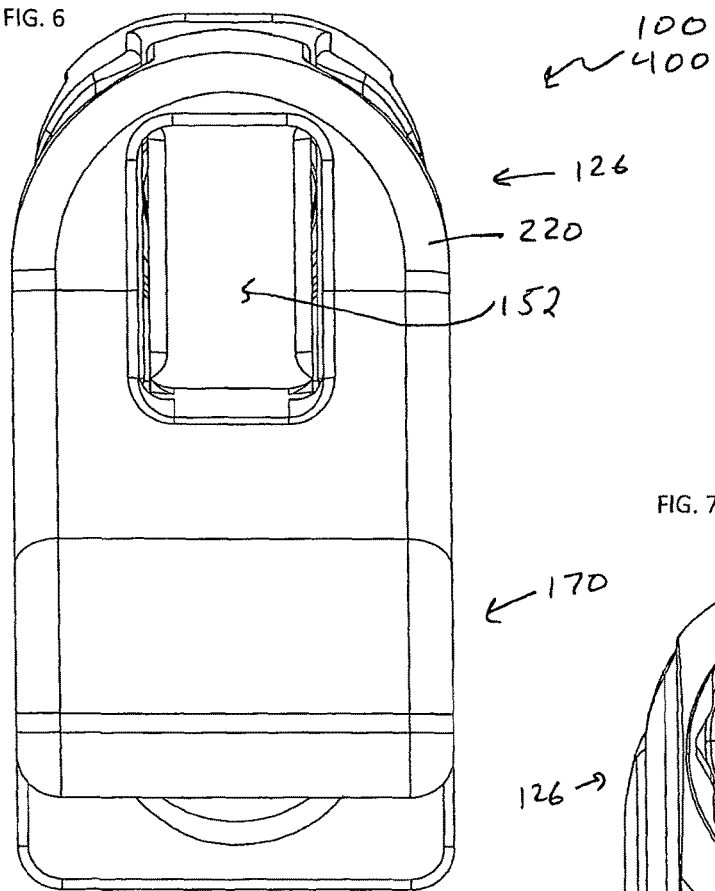
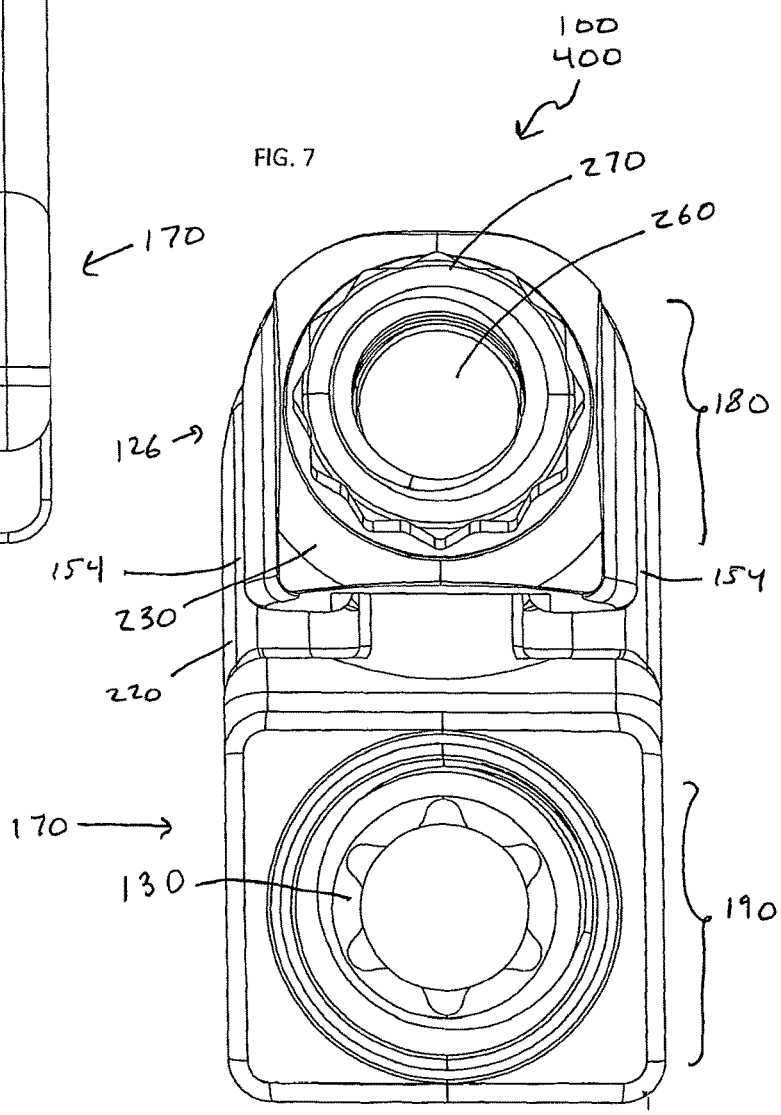

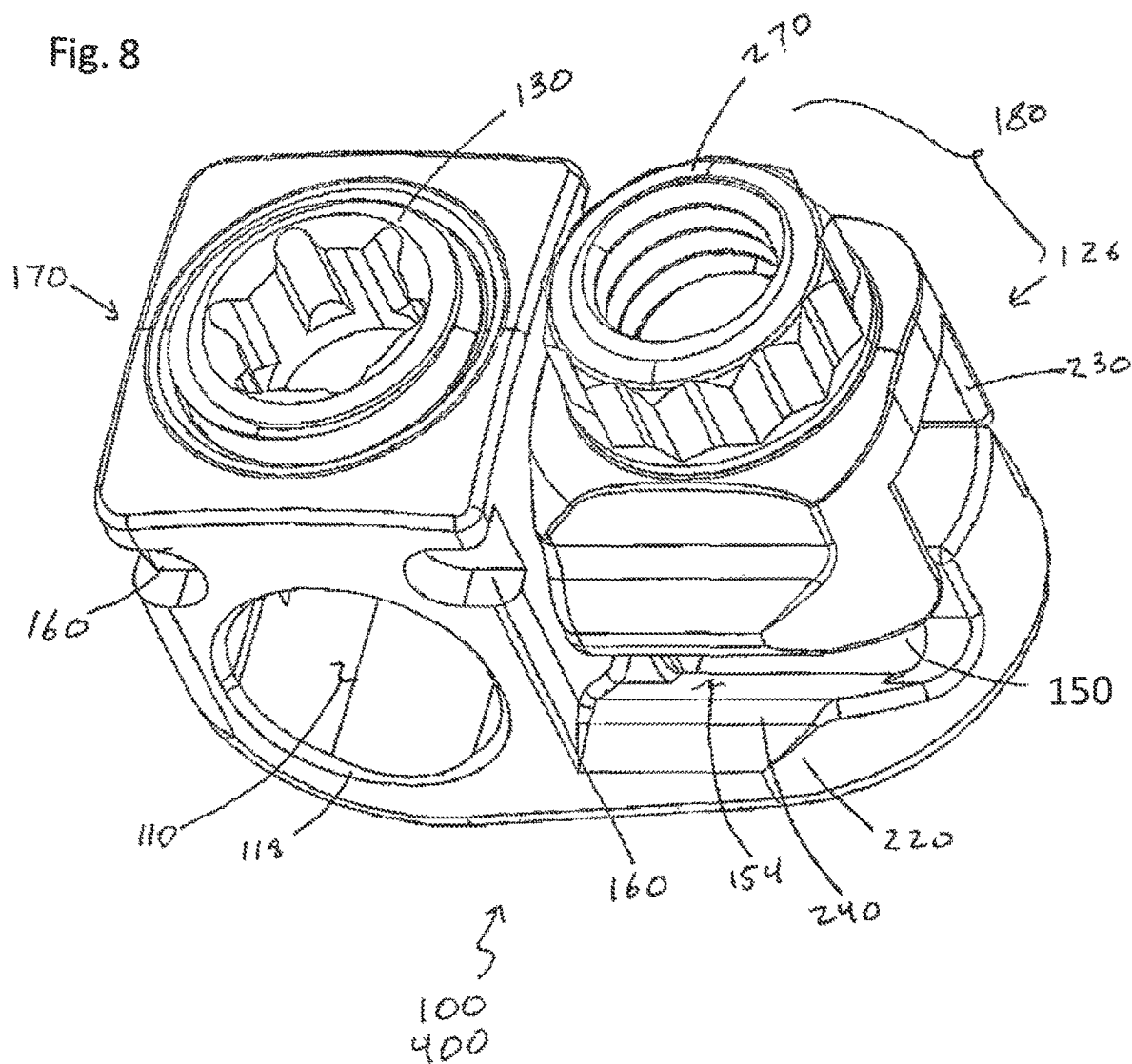

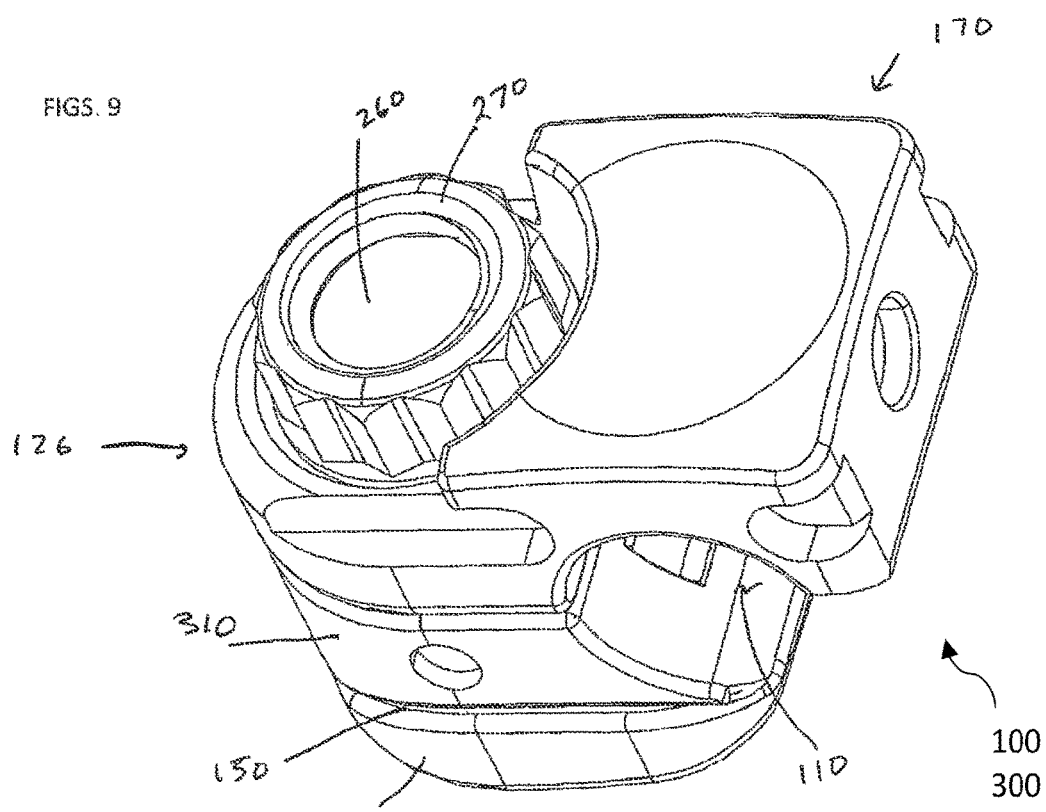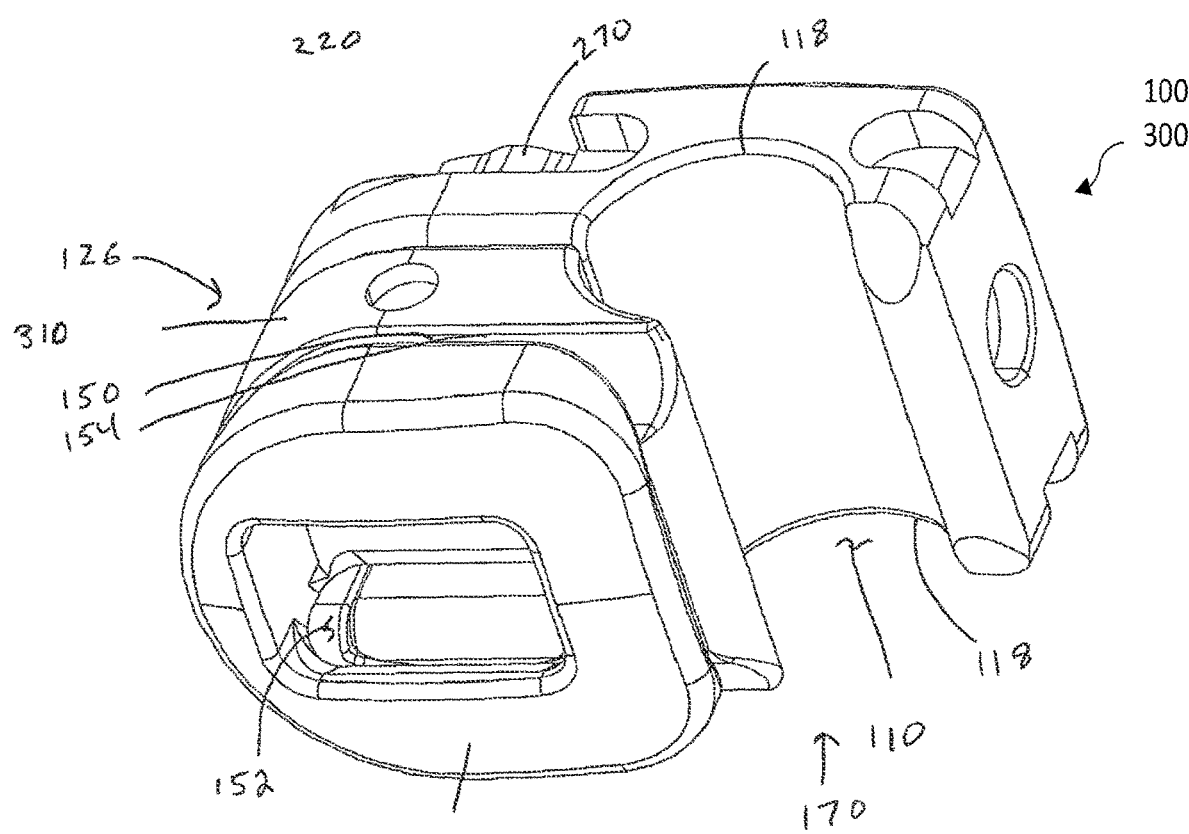

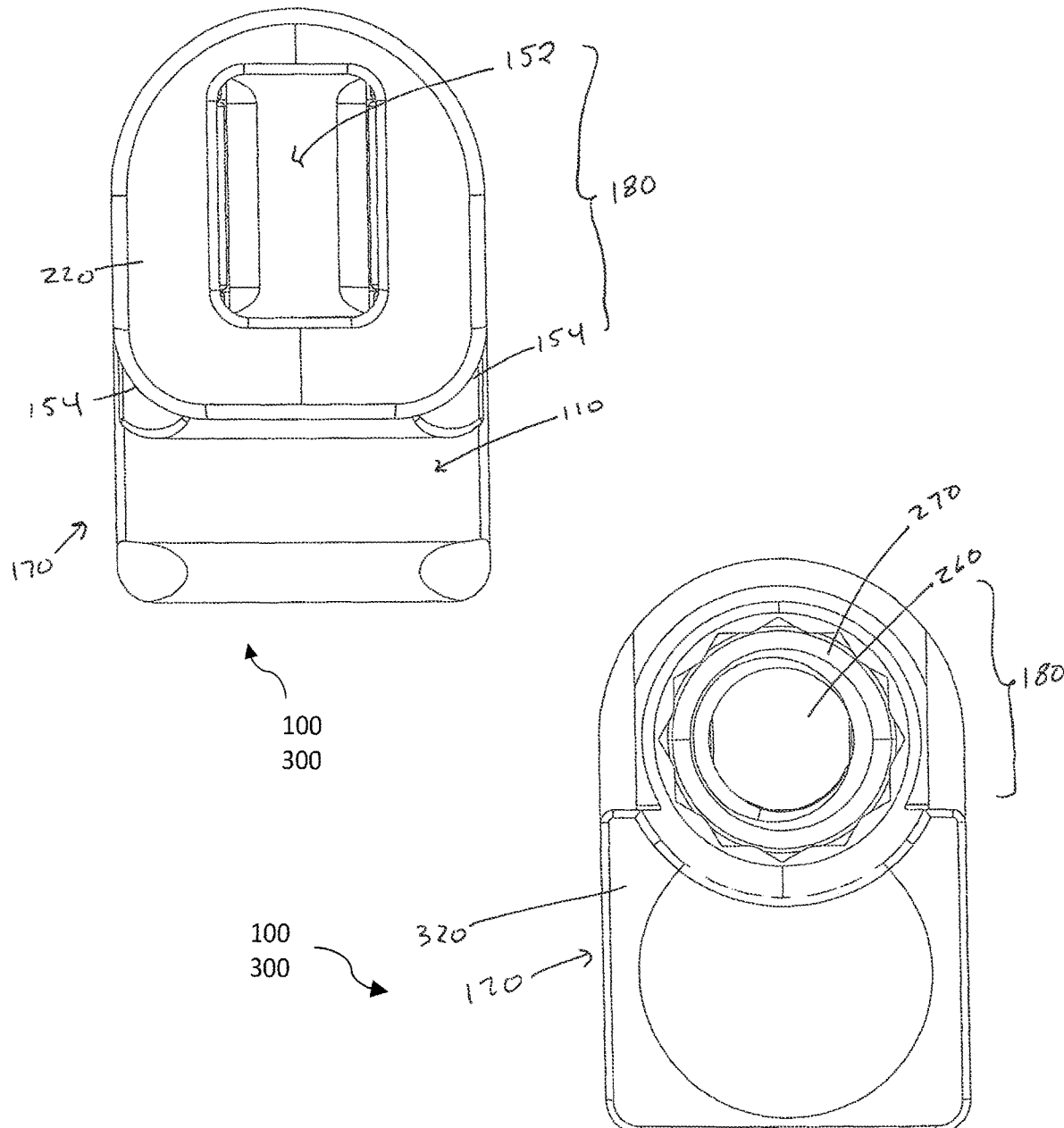

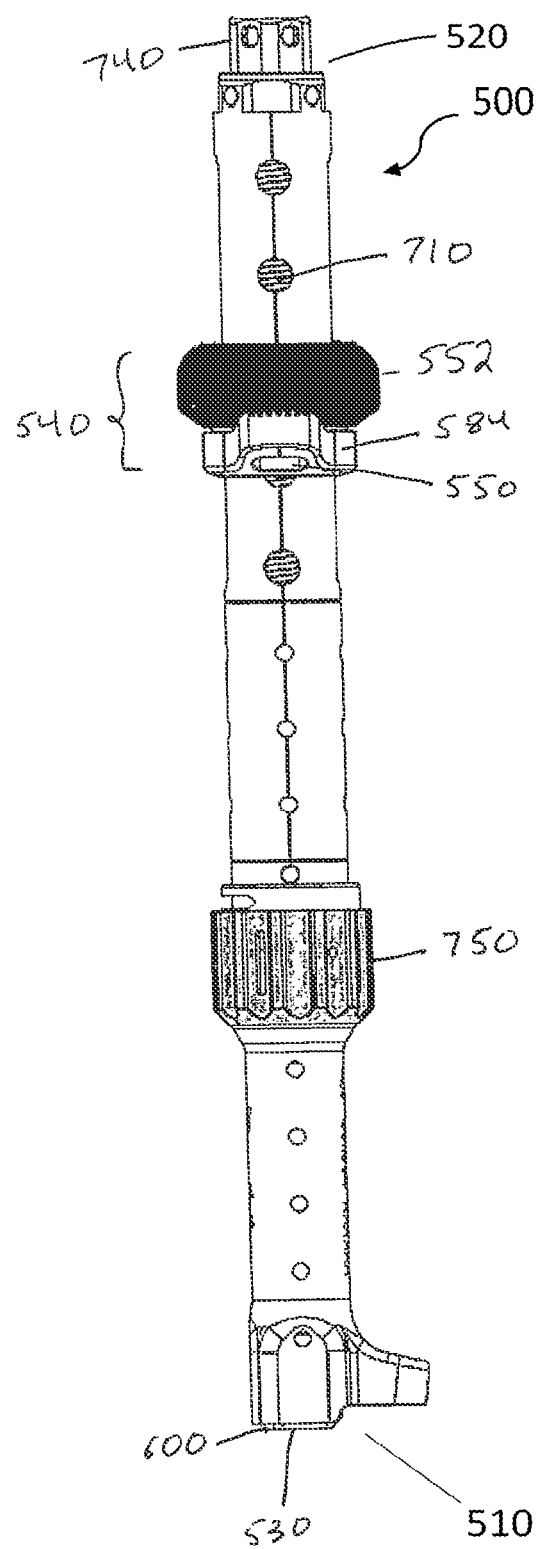
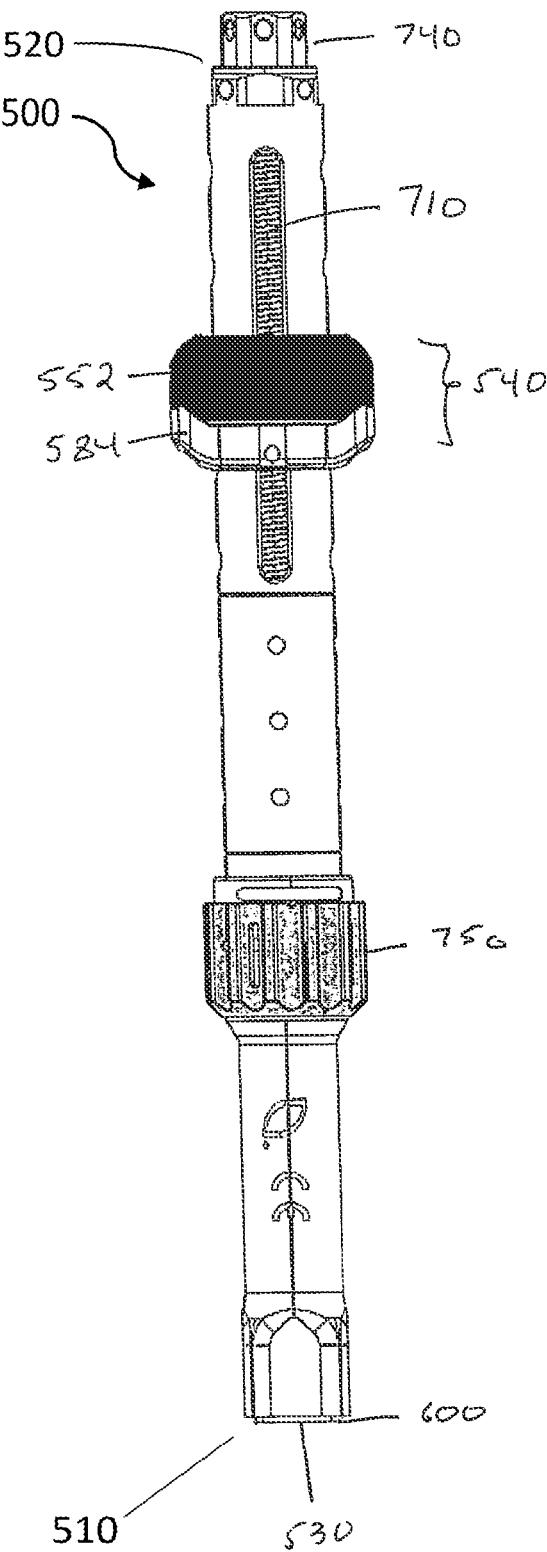
FIG. 18
FIG. 19

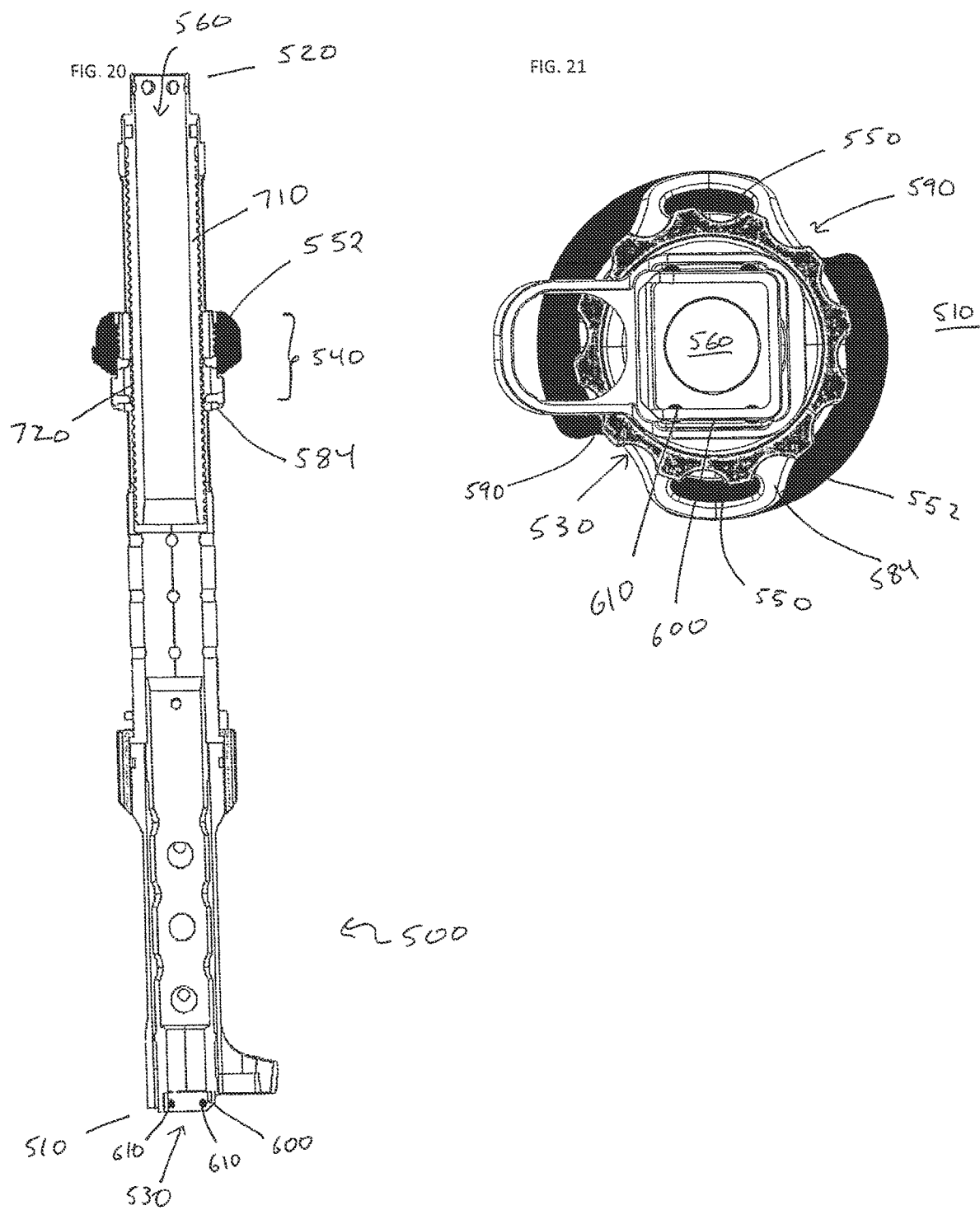

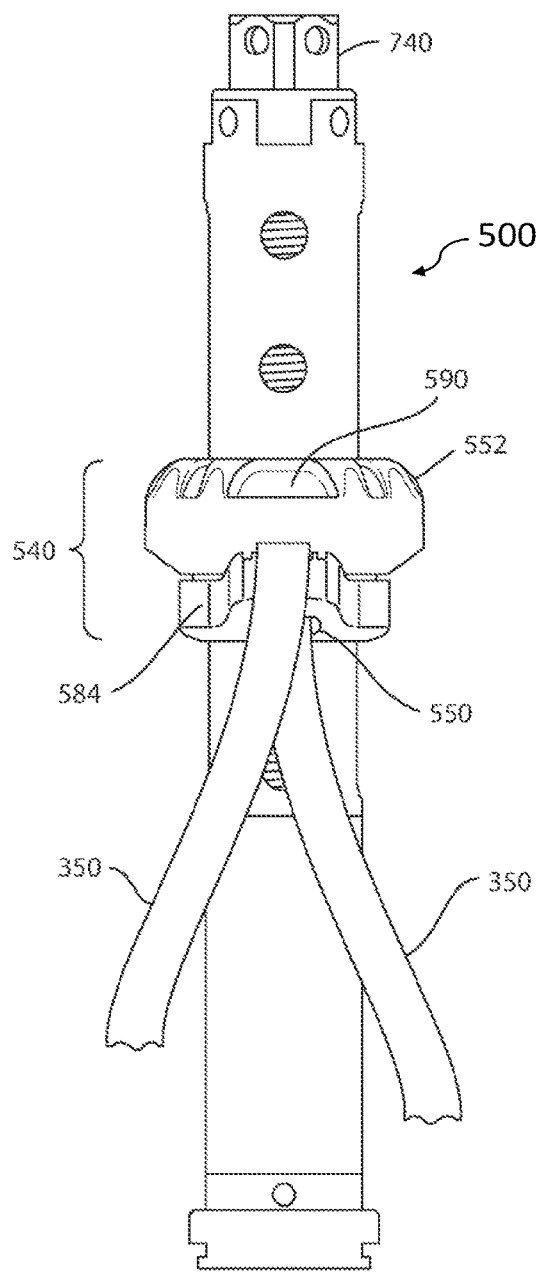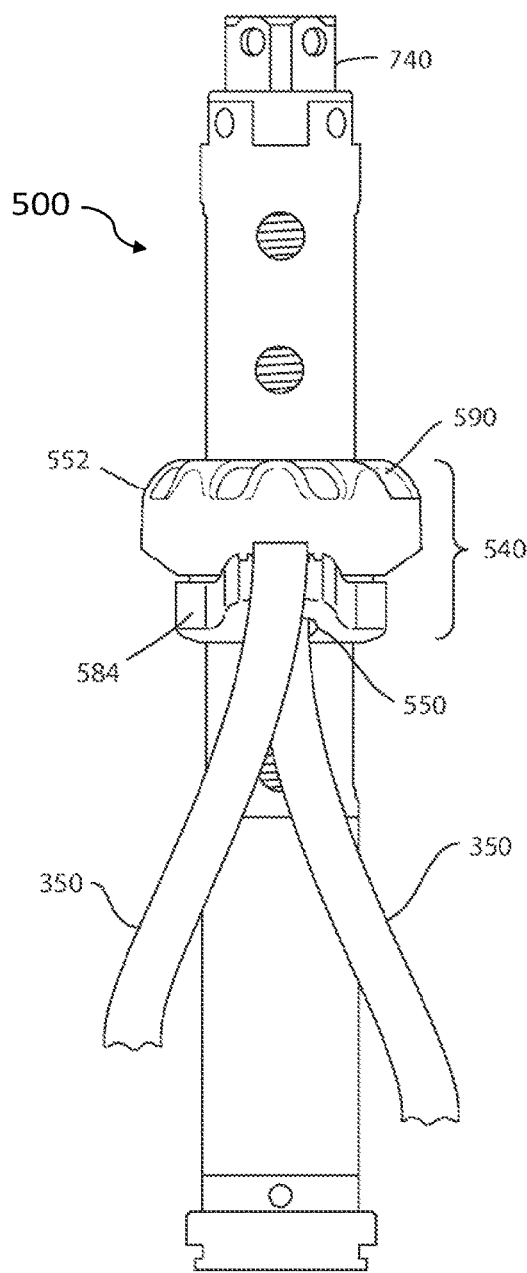

SURGICAL BAND CLAMP SYSTEM

CROSS REFERENCE TO RELATED APPLICATIONS

This application is a continuation of U.S. patent application Ser. No. 16/391,724 filed Apr. 23, 2019, which is a continuation of U.S. patent application Ser. No. 15/368,279 filed Dec. 2, 2016, the contents of which are entirely incorporated herein by reference.

FIELD

The present disclosure relates generally to medical devices, more specifically to the field of spinal surgery and spinal fixation devices. Such devices as well as systems and methods for use therewith are described.

BACKGROUND

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

Surgical procedures on the spine often include the immobilization of two or more vertebra. Immobilizing the vertebrae may be accomplished in many ways (e.g. fixation plates and pedicle screw systems). One of the most common methods for achieving the desired immobilization is through the application of bone anchors (most often introduced into the pedicles associated with the respective vertebra to be fixed) that are then connected by rigid rods locked to each pedicle screw. These pedicle screw systems are very effective. Pedicle screws generally include an anchor component and a rod-housing component.

However, in some cases screws are not the best choice for a spinal bone anchor. Some bone structures might not have sufficient mechanical strength or integrity to withstand penetration by the screw, due to injury or age-related deterioration. In some cases it may be desirable for the bone anchor to have a small degree of freedom of movement relative to the bone structure, which cannot be provided by bone screws. Still in some other cases it may be desirable to provide stability to an adjacent vertebra or multiple vertebrae adjacent to a vertebra being immobilized with a fixation construct, yet without fully immobilizing the adjacent vertebra. As a result, there is a need in the art for alternative fastening means for bone anchors.

SUMMARY

The needs above, as well as others, are addressed by embodiments of a connector system for securing a spinal rod to a bone structure via a band clamp described in this disclosure (although it is to be understood that not all needs described above will necessarily be addressed by any one embodiment).

Dual-lock connectors are provided with separate locking mechanisms for the band that connects the connector to the bone structure and for the spinal rod. A general embodiment of the dual lock connector comprises: a rod channel dimensioned to admit the spinal rod; a locking cap channel intersecting the rod channel; a locking cap in the locking cap channel; a pair of band channels each having a band entrance and a band exit; and a clamping mechanism that modulates the width of at least a portion of each of the pair of band channels.

A single-lock connector is provided that has one locking mechanism for the band that connects the clamp to the bone structure and for the spinal rod. A general embodiment of the single-lock connector comprises a base having a band entry channel and a band friction surface; a threaded post fastened to the base, such that the base cannot translate in the distal/proximal direction relative to the threaded post; a nut on the threaded post; an upper housing section between the nut and the base, having an upper rod channel portion; and a lower housing section between the upper housing section and the base, having a lower rod channel portion that forms a partially cylindrical rod channel in combination with the upper rod channel portion, and a band friction countersurface that forms a pair of band exit channels contiguous with the band entry channel in combination with the base; wherein tightening the nut imparts compressive force on the upper section with a distal vector, which causes the upper section to exert compressive force on the lower section with a distal vector, which in turn causes the lower section to exert compressive force on the base with a distal vector.

A tensioning instrument for use with the connectors described above is provided. The tensioning instrument functions to control the tension on the band connecting the connector to the bone and can be used through relative small surgical incisions. A general embodiment of the tensioning instrument comprises a distal end and a proximal end; a connector engagement feature on the distal end; a band holder configured to reversibly connect to a band and restrict longitudinal translation of the band relative to the band holder, the band holder comprising a band connection ring comprising a pair of band slots for holding the flexible band, and a band locking ring abutting the band connection ring, capable of at least limited rotation relative to the band connection ring, comprising a pair of indentations sufficiently deep to allow the flexible band to enter and exit the pair of band slots without friction from the band locking ring when the indentations are aligned with the band slots, and a pair of surfaces that exert friction on the flexible band sufficient to prevent longitudinal translation of the flexible band relative to the band holder when aligned with the pair of band slots; and a band holder translation mechanism to control the translation of the band holder relative to the connector engagement feature.

The band clamp and associated band may be used as an alternative means to connect a spinal rod to a bone. For example, the band may be passed under the lamina to form a loop therearound with the band clamp sitting above the lamina and coupled to the rod. The band could similarly be looped around a transverse process or rib, for example. Alternatively, the connector and associated band may used to strengthen, reconstruct, and/or otherwise emulate ligaments that may have been damaged or removed during implantation of the fixation construct. For example, a band connected to the connector may be wrapped around the facet, transverse process, lamina, rib and/or spinous process to provide further stability to the construct. In still another alternative, the connector and associated band may be used to provide additionally stability to the spine adjacent a fixation construct. For example, the band may be wrapped around (or, through a hole formed therein) one or more of a lamina(s), transverse process(es), spinous process(es), and rib(s) of one or more vertebrae proximal to the end of the construct.

A method of anchoring a spinal rod housing to a bone structure with a band clamp is provided. A general embodiment of the method comprises positioning a flexible band around a bone structure to make contact between a middle portion of the band and said bone structure; connecting a pair of terminal portions of the flexible band to a connector, the connector comprising a pair of band channels and the spinal rod housing, wherein each of the pair of terminal portions is in a respective band channel; increasing tension on the flexible band in an amount sufficient to cause contact between the connector and the bone structure and sufficient to restrict movement of the connector relative to the bone structure; locking each of the terminal portions of the flexible band the connector by narrowing each of the band channels to prevent release of the tension; and immobilizing the spinal rod in the spinal rod housing to prevent movement of the connector relative to the spinal rod.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 5A. A front plan view of the connector shown in FIG. 1 in which the band clamping mechanism is in an open position.

FIG. 5B. A front plan view of the connector shown in FIG. 1 in which the band clamping mechanism is in closed position.

FIG. 6. A bottom plan view of the connector shown in FIG. 1.

FIG. 7. A top plan view of the connector shown in FIG. 1.

FIG. 8. A perspective view of an alternative embodiment of the connector having a closed rod channel.

FIG. 9. A perspective view of a single-lock embodiment of the connector.

FIG. 10. An alternative perspective view of the embodiment of the connector shown in FIG. 9.

FIG. 14. A bottom plan view of the connector shown in FIG. 9.

FIG. 15. A top plan view of the connector shown in FIG. 9.

FIG. 18. A side plan view of the embodiment of the tensioning instrument shown in FIG. 16.

FIG. 19. A front plan view of the embodiment of the tensioning instrument shown in FIG. 16.

FIG. 20. A side cross-sectional view of the embodiment of the tensioning instrument shown in FIG. 16.

FIG. 21. A bottom (distal) plan view of the embodiment of the tensioning instrument shown in FIG. 16, showing detail of the connector engagement features on the instrument.

FIG. 22. A partial side view of the embodiment of the tensioning instrument shown in FIG. 16, in which the indentations on the band locking ring are in alignment with the band slots on the band connection ring, to allow the flexible band to enter and exit the pair of band slots without friction from the band locking ring.

FIG. 23. A partial side view of the embodiment of the tensioning instrument shown in FIG. 16, in which the friction surfaces on the band locking ring are in alignment with the band slots on the band connection ring (and the indentations are not in alignment with the band slots), which would exert friction on the band.

DETAILED DESCRIPTION

Figure 1:
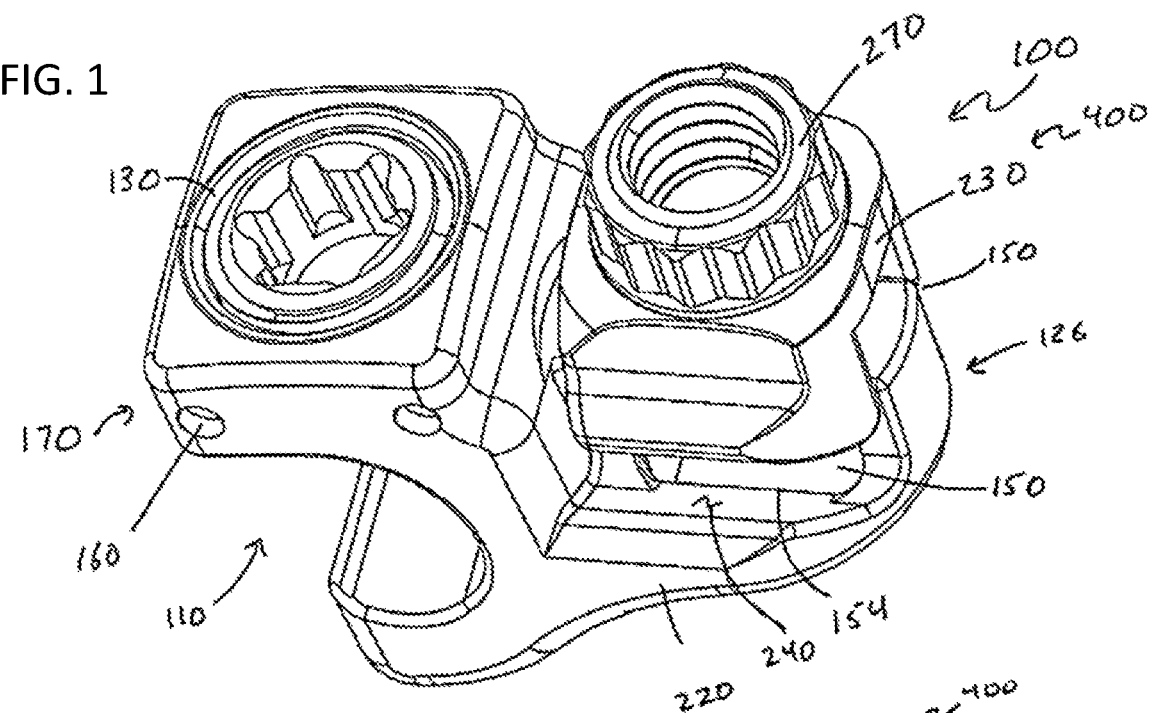
FIG. 1. A perspective view of a dual-lock embodiment of the connector.
Figure 2:
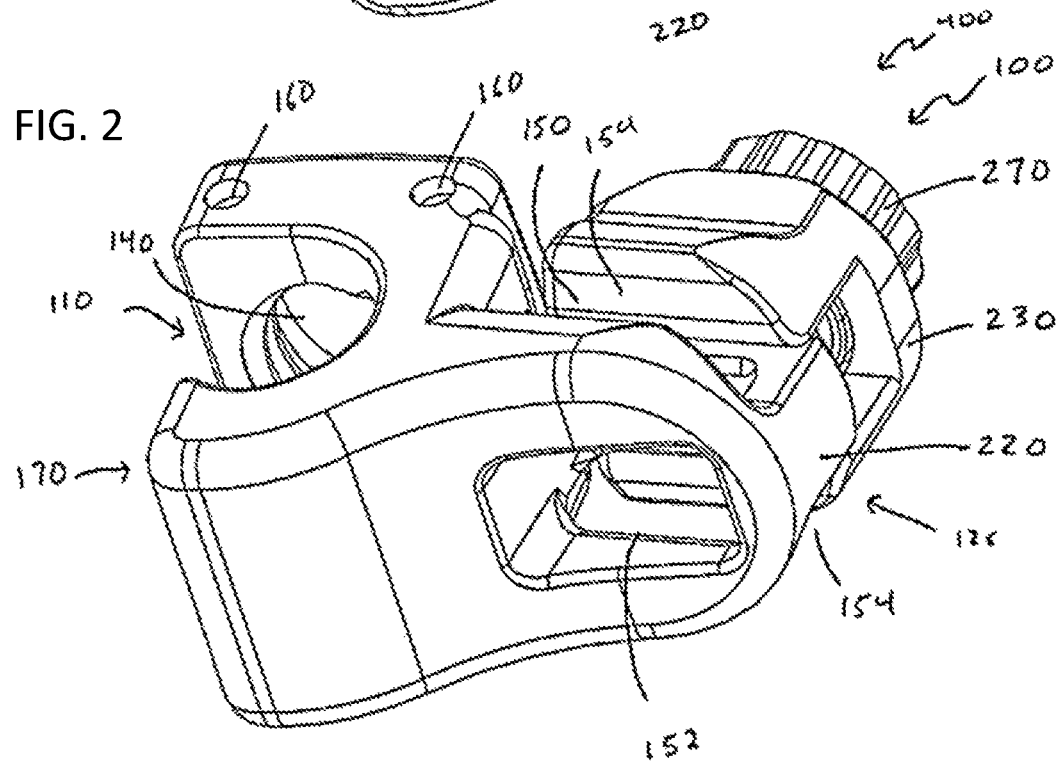
FIG. 2. An alternative perspective view of the embodiment of the connector shown in FIG. 1.
Figure 3A:
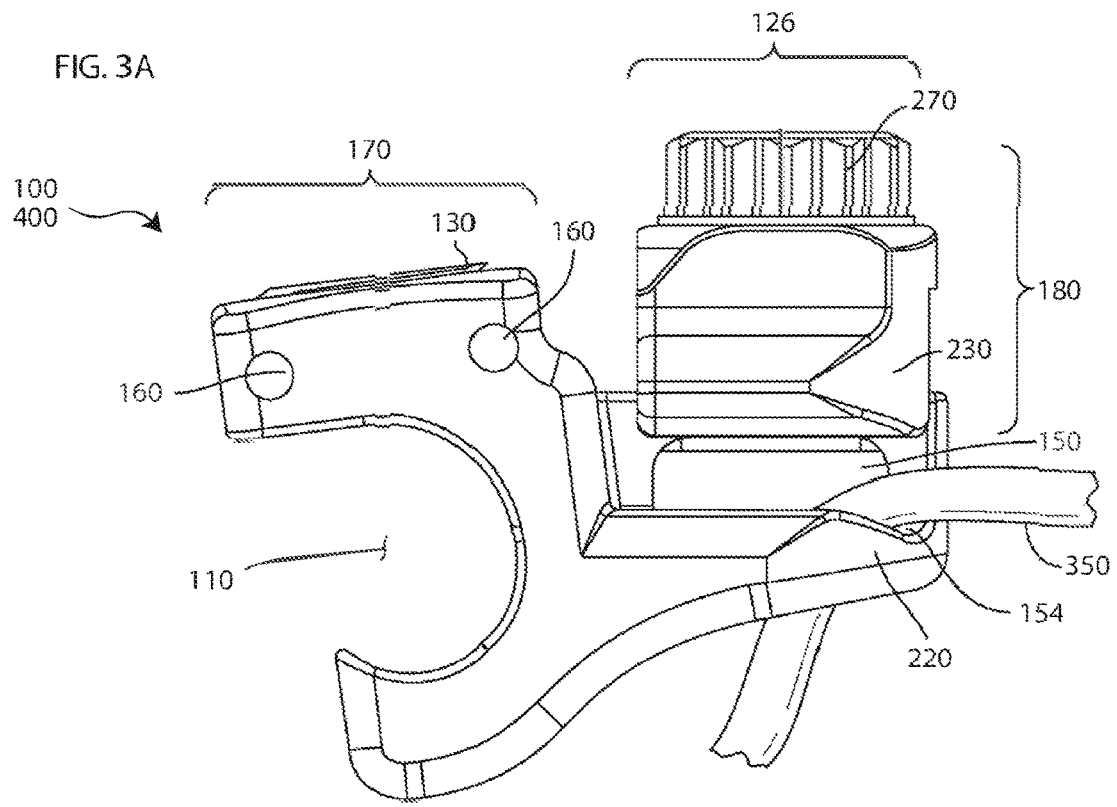
FIG. 3A. A side plan view of the connector shown in FIG. 1 in which the band clamping mechanism is in an open position.
Figure 3B:
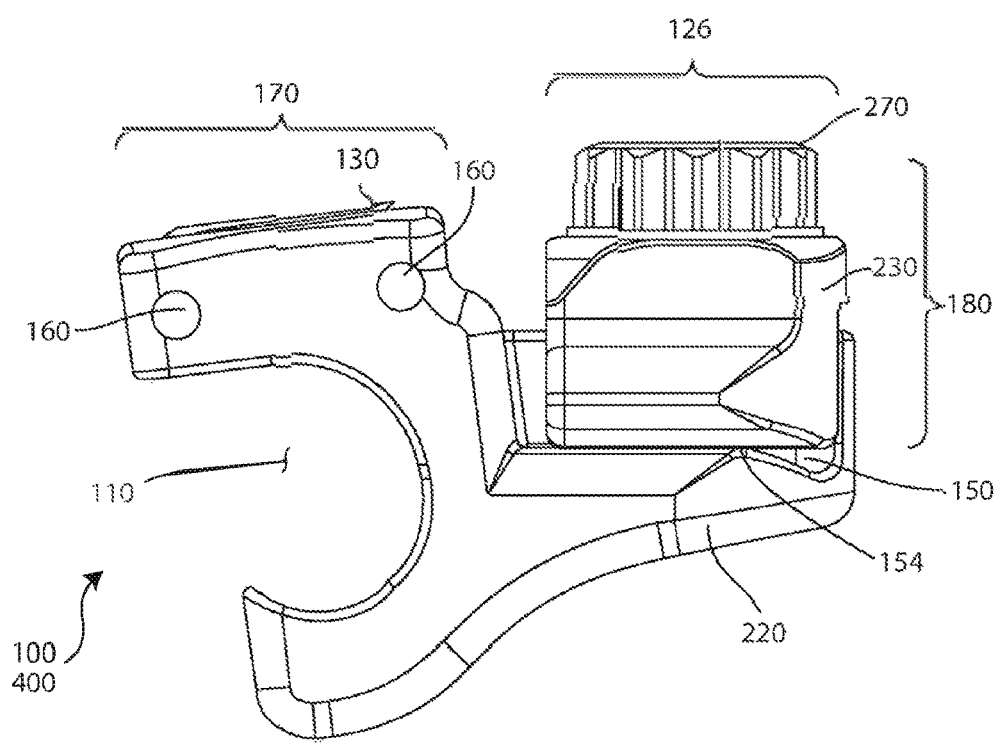
FIG. 3B. A side plan view of the connector shown in FIG. 1 in which the band clamping mechanism is in a closed position.
Figure 4:
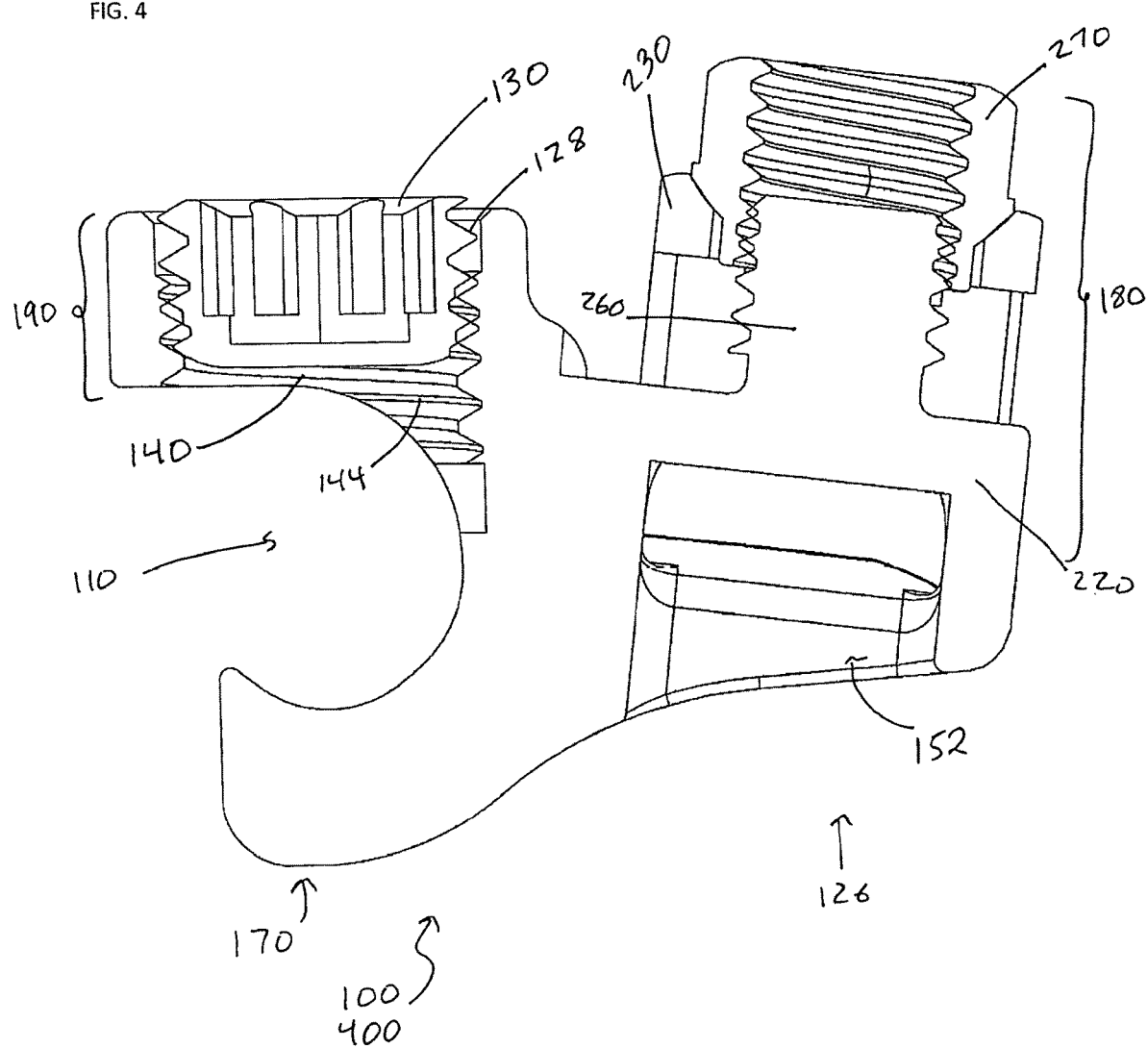
FIG. 4. A side cross-sectional view of the connector shown in FIG. 1.
Figure 11:
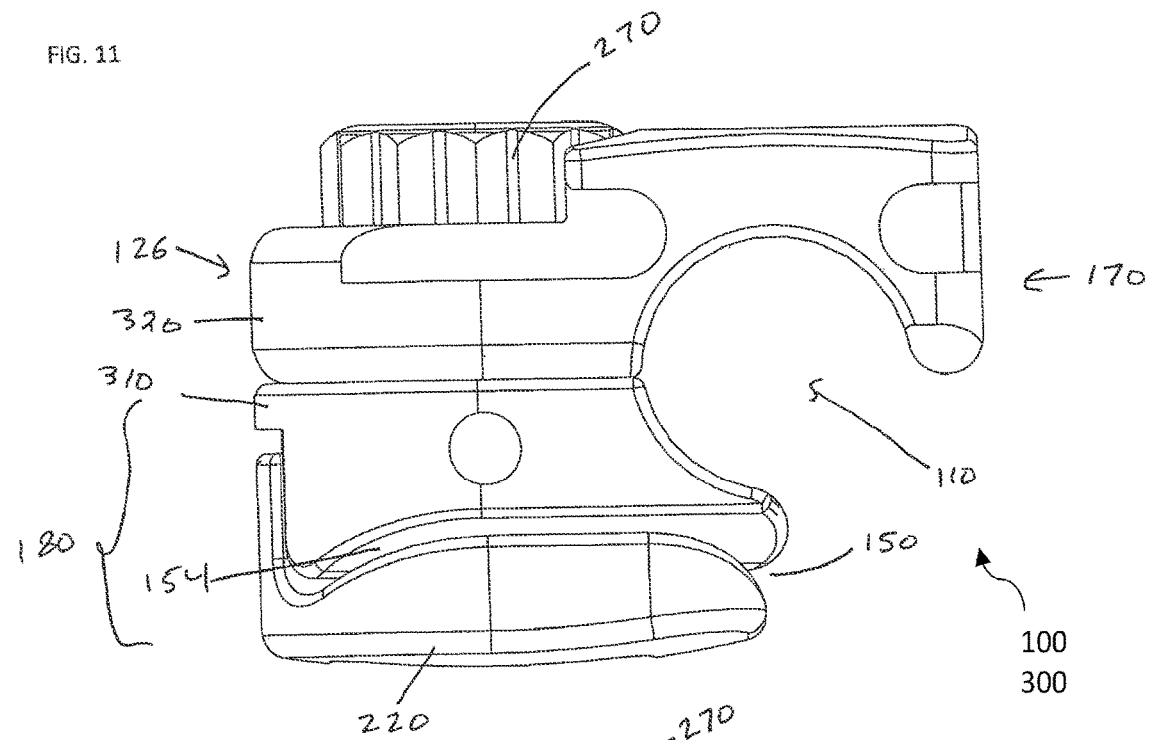
FIG. 11. A side plan view of the connector shown in FIG. 9.
Figure 12:
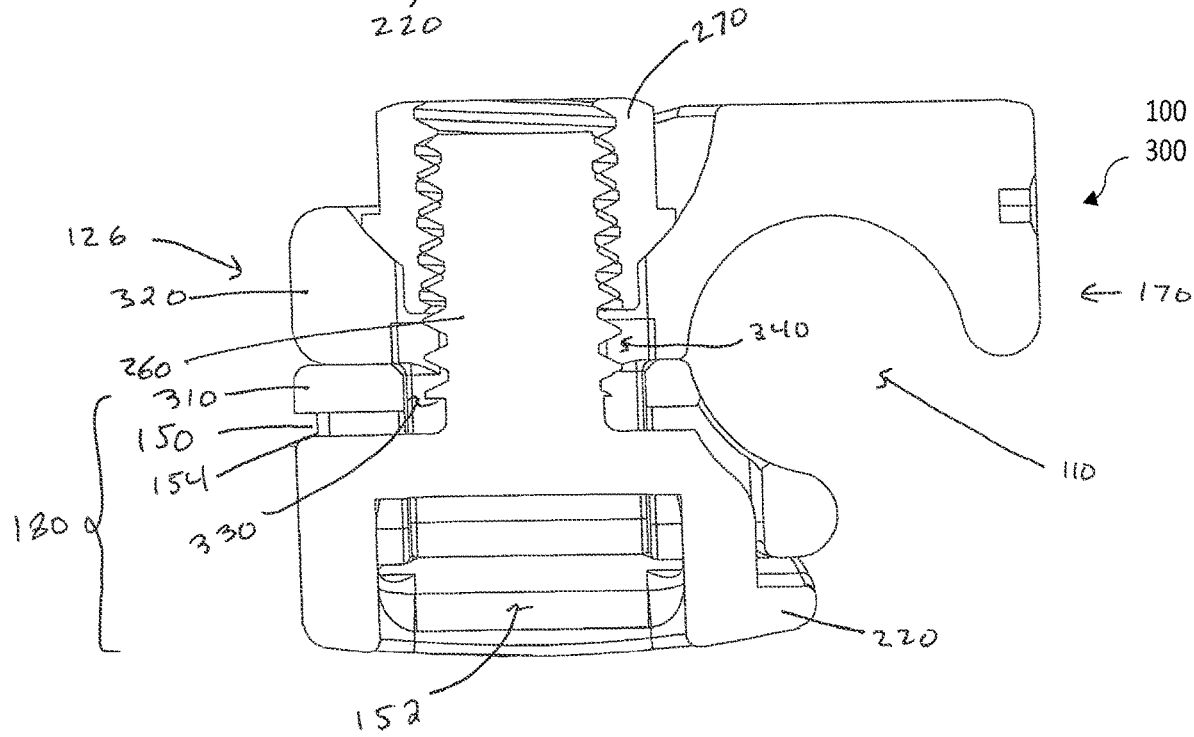
FIG. 12. A side cross-sectional view of the connector shown in FIG. 9.
Figure 13:
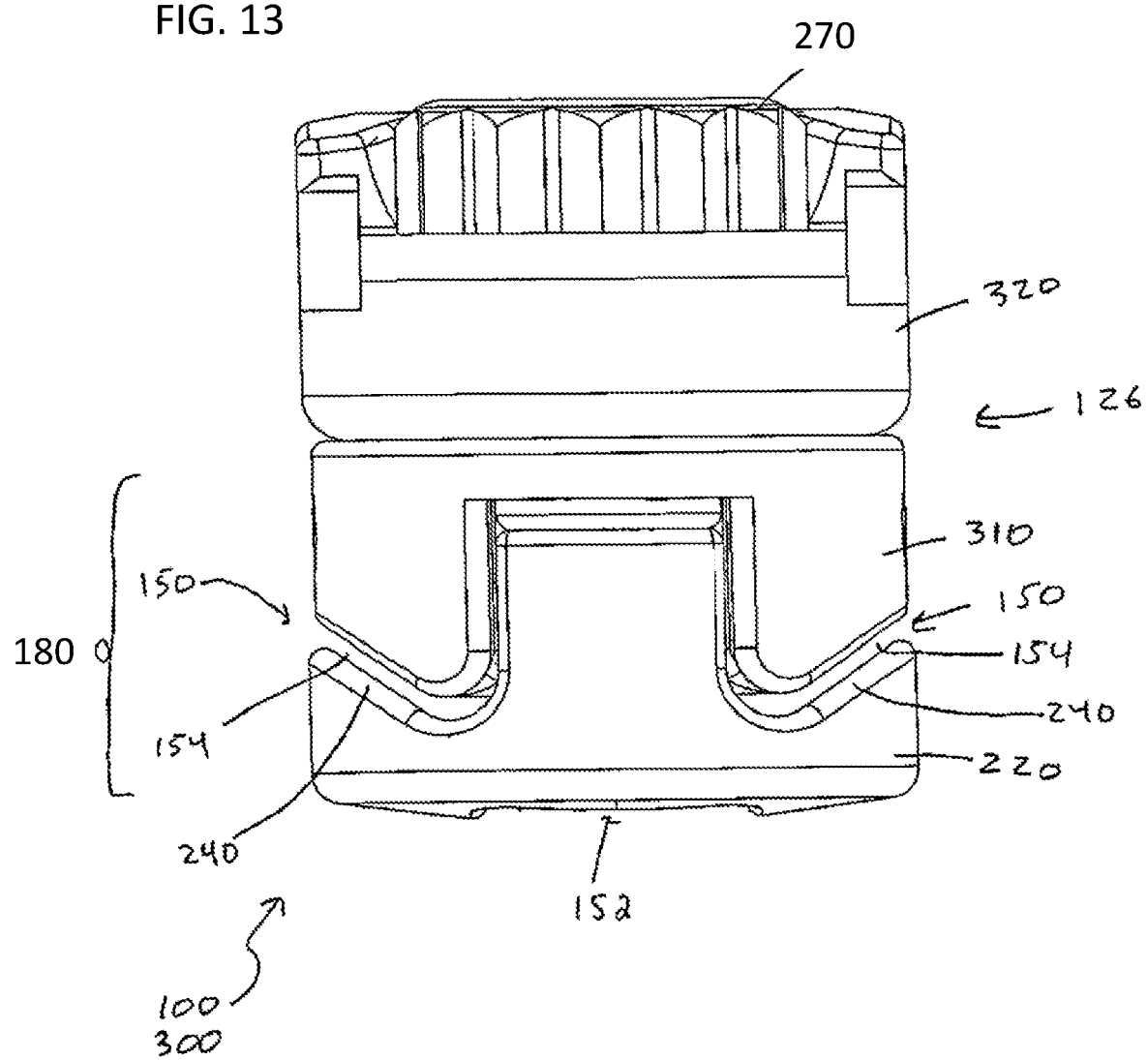
FIG. 13. A front plan view of the connector shown in FIG. 9.
Figure 16:
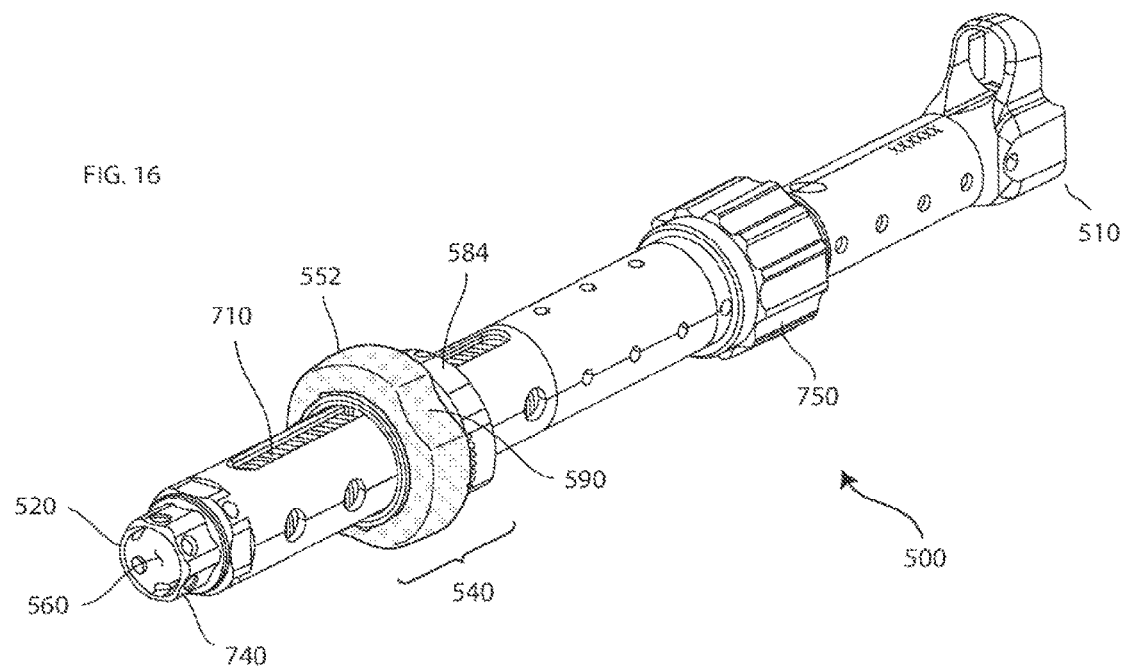
FIG. 16. A perspective view of an embodiment of the tensioning instrument.
Figure 17:
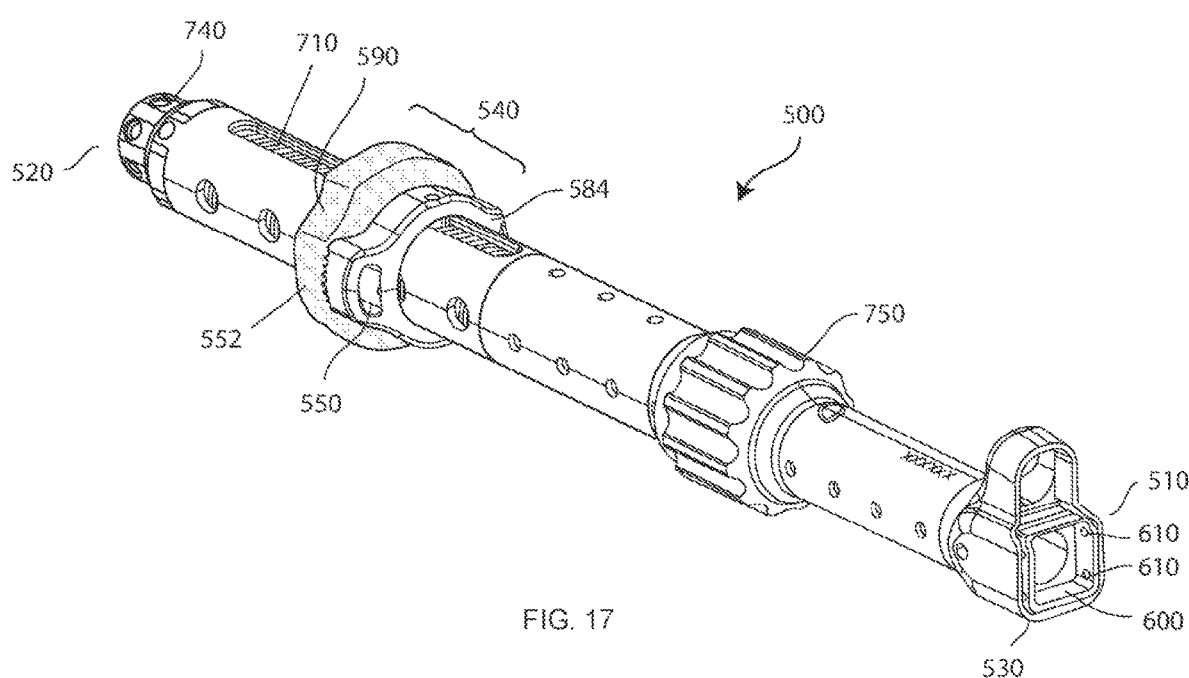
FIG. 17. An alternative perspective view of the embodiment of the tensioning instrument shown in FIG. 16.
Figure 24:
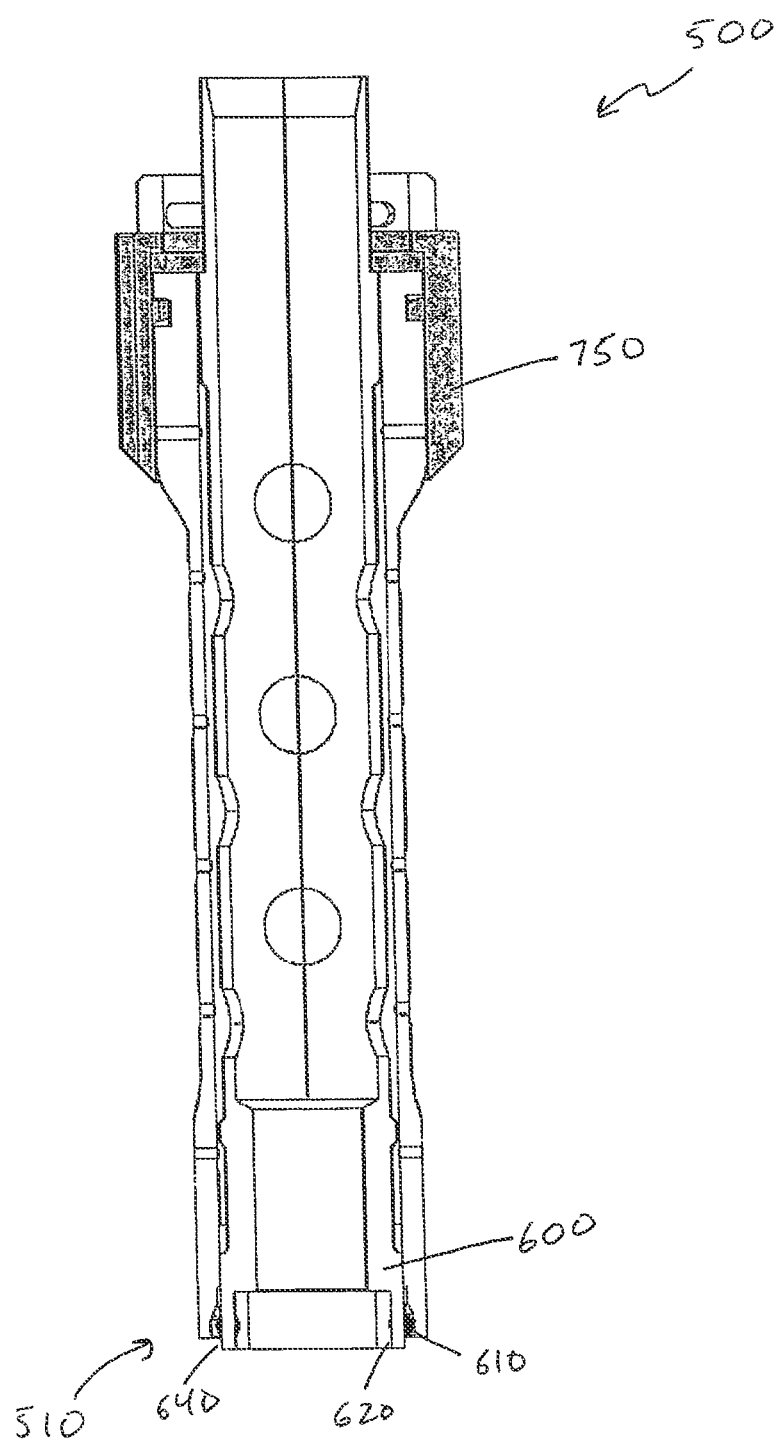
FIG. 24. A partial cross-sectional side view of the distal part of the embodiment of the tensioning instrument shown in FIG. 16, showing detail of the connector engagement feature.

Illustrative embodiments of a surgical band clamp system are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical band clamp system disclosed herein boasts a variety of inventive features and components that warrant patent protection, both individually and in combination.

A dual-lock version 400 of the connector 100 is shown in FIGS. 1-7. As shown, the connector 100 comprises: a rod channel 110 dimensioned to admit the spinal rod; a locking cap channel 140 intersecting the rod channel 110; a locking cap 130 in the locking cap channel 140; a pair of band channels 150 each having a band entrance 152 and a band exit 154; and a clamping mechanism 180 that modulates the width of at least a portion of each of the pair of band channels 150. The connector 100 can be roughly divided into a rod housing section 170 that contains the rod channel 110, locking cap channel 140, and locking cap 130; and a band clamp section 126 that contains the pair of band channels 150 and the clamping mechanism 180. The rod housing section 170 and the clamp section 126 can be laterally connected to each other to form the connector 100 as shown in FIGS. 1-2, 3A-3B, and 4. In the illustrated embodiments the rod channel 110 is separate from the band channels 150, and does not intersect with either of them. The dual-lock embodiments 400 have the advantage of allowing the tension on the band 350 to be adjusted regardless of whether the connector 100 has been secured to the rod (and vice versa).

The locking cap 130 and locking cap channel 140 each have complementary engagement features. In a specific embodiment, the locking cap 130 comprises a screw thread 128 on its exterior and the locking cap channel 140 comprises complementary threads 144. The engagement features on the locking cap 130 and locking cap channel 140 function to guide the locking cap 130 in the distal direction to contact and exert distal force on the spinal rod. In the context of this disclosure the term "distal" refers to the direction away from the user (e.g., surgeon) during implantation of the connector 100, whereas "proximal" refers to the opposite direction toward the user. In some cases the locking cap 130 or locking cap channel 140 (or both) will contain locking features to prevent the locking cap 130 from translating in the proximal direction once full reduced against the spinal rod.

In the embodiment illustrated in FIGS. 1-7 the band clamp section 126 contains a pair of band clamp channels 150 which share a common band entrance 152 and each of which has a distinct band exit 154. In use, the two terminal sections of the band 350 are passed through the distal band entrance 202 after being wrapped around the bone structure 14 (e.g. a lamina), and each of the two terminal sections is threaded through the band channels 150 to its respective band exit 154 (to one side or another). The illustrated clamping mechanism 180 is formed by two opposing bodies that together define part of the band channels 150, and can be repositioned to modulate the width of the band channels 150 and exert friction against the bands when in place. The two opposing bodies are a base 220 and a separate compressing body 230. In the illustrated embodiment the base 220 is integral with the rod housing section 170, which has the advantage of simplicity in manufacturing. However, the base 220 and the rod housing section 170 may be fabricated separately and assembled, as necessary for the particular application. The proximal surface of the base 220 functions as a compressing surface 240 to counter force exerted by the compressing body 230. A mechanism is provided to exert force with a distal vector on the compressing body 230, which in turn exerts force with a distal vector on the base 220 (and on the band if it is present in the band channel 150). In the illustrated embodiment, this mechanism comprises a threaded post 260 that does not translate along the longitudinal axis relative to the base 220 and a nut 270 on the threaded post 260 that is positioned to press on the compression body 230 when the nut 270 is tightened on the threaded post 260. By tightening the nut 270 the compressing body 230 is moved toward the base 220, and the two band channels 150 are narrowed. This action can be seen by comparing the connector 100 with the clamping mechanism 180 in the open position in FIGS. 3A and 5A to the connector 100 with the clamping mechanism 180 in the closed position in FIGS. 3B and 5B. Ultimately the band will be in contact with both the base 220 and the compressing body 230, and the band 350 can be locked in place by further tightening the nut 270 on the post 260.

The embodiment of the connector 100 shown in FIGS. 1-7 is constructed from three separate pieces: a main body 280 that contains the rod channel 110, the locking cap channel 140, the base 220, and the threaded post 260; the nut 270 on the threaded post 260; and the compressing body 230 around the threaded post 260 between the nut 270 and the base 220. In order for the connector 100 to function correctly these three pieces must translate relative to one another, and this can be accomplished by providing these components separately. Although in the illustrated embodiments each of the three pieces is a unitary structure, each could be constructed from at least two smaller pieces fastened together.

In some embodiments of the connector 100 the nut 270 is a locknut. The locknut is a nut with some means of resisting removal or loosening due to vibration and/or torque. In some embodiments of the connector 100 the locknut is a nut 270 used in conjunction with a spring lock washer (thus the nut on its own is not resistant to loosening). In further embodiments the locknut is structured to resist loosening on its own; examples of such locknuts include a castellated nut, distorted thread locknut, centerlock nut, elliptical offset locknut, toplock nut, Philidas nut, interfering thread nut, tapered thread nut, jam nut, jet nut, Keps nut, plate nut, polymer insert nut, security lock nut, serrated face nut, serrated flange nut, speed nut, split beam nut, and palnut.

The exterior of the housing 170 near the proximal end of the locking cap channel 140 may include instrument attachment features 160 for coupling to various tools useful during implantation of the bone anchor and associated fixation tool(s)construct (e.g., inserters, reducers, and other such tools as are known in the art). In the specific embodiment shown in FIGS. 1-8, the attachment features 160 comprise four depressions near the corners. Together the four depressions allow a tool to connect to the connector 100 in such a way that the tool will neither translate longitudinally nor rotate circumferentially while attached. Other configurations of course may be used.

The rod channel 110 is open on one lateral side in the embodiments of the connector 100 shown in FIGS. 1-7. This allows the spinal rod to be loaded into the rod channel 110 from a lateral direction, thus having the advantage of ease of installation. However, other configurations of the rod channel 110 are possible. Another example is shown in FIG. 8. FIG. 8 shows an embodiment of the connector 100 in which the rod channel 110 is open only at longitudinal ends 118 (i.e., along the longitudinal axis of the spinal rod), and is closed on all lateral sides. Such embodiments of the connector 100 have the advantage of enhanced stability once the rod is in place and potentially smaller size.

An alternative general embodiment of the connector 100 is shown in FIGS. 9-15. The "single-lock" connector 300 unifies the band clamping mechanism 180 and the rod clamping mechanism 190. This has the advantage of allowing the band 350 to be locked in place and the rod to be locked in place in a single step. As in the embodiments described above, the single-lock clamp 300 comprises a base 220 and a threaded post 260 fastened to the base 220; the term "fastened" when referring to the post 260 and the base 220 may include embodiments in which the post 260 and base 220 are part of the same integral structure. In all contemplated embodiments the threaded post 260 and the base 220 cannot translate in the longitudinal axis relative to one another.

In the illustrated embodiment the base 220 comprises a single band entrance 152 for both band channels 150, and two band exits 154.

A nut 270 may be engaged to the threaded post 260, which may be any version of a nut 270 disclosed as suitable above for the dual-lock embodiments 400.

The single-lock embodiment 300 comprises a lower housing section 310, which functions like the compressing body 230 in the dual-lock embodiments 400 in that it moves relative to the base 220 to modulate the width of the band channels 150 and exert distal force on the band segments when they are present. In the illustrated embodiment the lower housing section 310 is placed around the threaded post 260; it contains an aperture 330 to admit the post 260 (not shown). The lower housing section 310 forms the distal part of the rod channel 110.

Between the lower housing section 310 and the nut 270 is an upper housing section 320. The upper housing section 320 forms the proximal part of the rod channel 110. In the illustrated embodiment the upper housing section 320 is placed around the threaded post 260, and has an aperture 340 to admit the post 260.

The upper housing section 320, lower housing section 310, and base 220 are all free to translate along the longitudinal axis relative to one another when the nut 270 has not been tightened (the connector 100 is referred to as "loose" in this state). While the connector 100 is loose, the width of the rod channel 110 may be increased for the easy insertion of the spinal rod. Once the spinal rod is inserted into the rod channel 110, the nut 270 is tightened, causing the rod channel 110 to narrow until the rod is locked into place. Likewise, while the connector 100 is loose the terminal regions 360 of the band 350 can be pulled through the band channel 150 without significant friction being exerted by the lower housing section 310 and the base 220. Once the band 350 has been threaded through the band channel 150 and adjusted to the desired tension, the nut 270 is tightened causing the band 350 to be clamped between the base 220 and the lower housing section 310.

A tensioning instrument 500 for use with the system is also provided; an embodiment of which is shown in FIGS. 16-26. The tensioning instrument 500 allows tension on the band 350 between the bone structure and the connector 100 to be precisely modulated without creating a large incision during-surgery. A general embodiment of the tensioning instrument 500 comprises a distal end 510 and a proximal end 520; a connector engagement feature on the distal end 510; a band holder 540 configured to reversibly connect to a band 350 and restrict longitudinal translation of the band 350 relative to the band holder 540, the band holder 540 comprising a band connection ring 584 comprising a pair of band slots 550 for holding the flexible band 350; and a band locking ring 552 abutting the band connection ring 584, capable of at least limited rotation relative to the band connection ring 584, comprising a pair of indentations 590 sufficiently deep to allow the flexible band 350 to enter and exit the pair of band slots 550 without friction from the band locking ring 552 when the indentations 590 are aligned with the band slots 550, and a pair of surfaces that exert friction on the flexible band 350 sufficient to prevent longitudinal translation of the flexible band 350 relative to the band holder 540 when aligned with the pair of band slots 550; and a band holder translation mechanism to control the translation of the band holder 540 relative to the connector engagement feature 530. The instrument 500 is generally elongate in shape, and may further comprise an internal lumen 560 running from the proximal end 520 to the distal end 510 and dimensioned to admit any of various useful tools, such as a nut driver.

The connector engagement feature 530 will be designed to restrict or prevent the degree of movement between the tensioning instrument 500 and the connector 100 when engaged. In this context "restricted" movement refers to a reduction in possible movement that is significant, but not necessarily complete or absolute. The connector engagement feature 530 may include a clamp locking mechanism capable of reversibly locking the connector 100 to the connector engagement feature 530 to restrict both translation and deflection of the tensioning instrument 500 relative to the connector 100, granting stability during the tensioning process. Some embodiments of the connector 100 may comprise one or more instrument attachment features 160, as explained above. Exemplary embodiments of the tensioning instrument 500 may comprise a connector engagement feature 530 that engages with an instrument engagement feature 160 on the connector 100.

Figure 25:
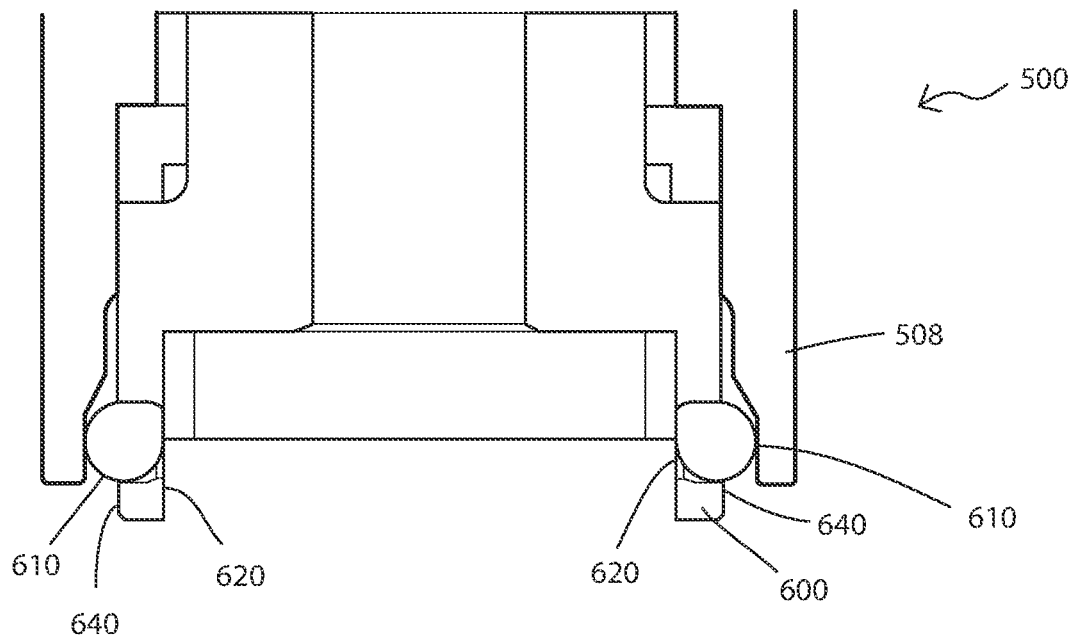
FIG. 25. A partial cross-sectional side view of the distal part of the embodiment of the tensioning instrument shown in FIG. 16, showing detail of the connector engagement feature in the unlocked configuration.
Figure 26:
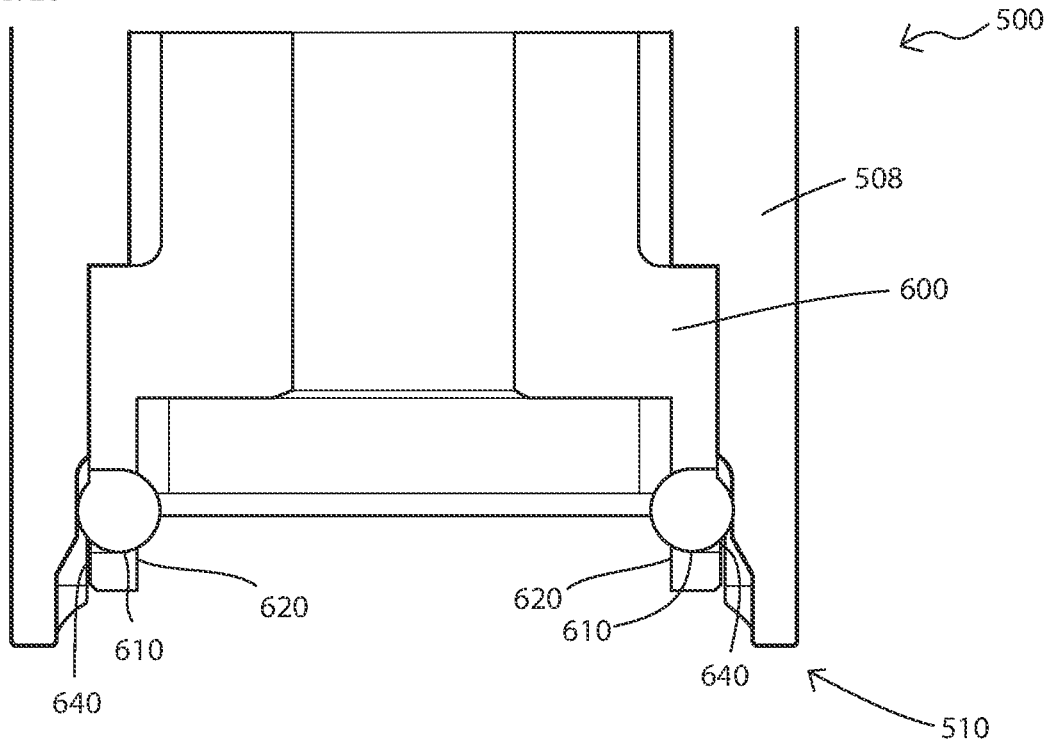
FIG. 26. A partial cross-sectional side view of the distal part of the embodiment of the tensioning instrument shown in FIG. 16, showing detail of the connector engagement feature in the locked configuration.
Figure 27:
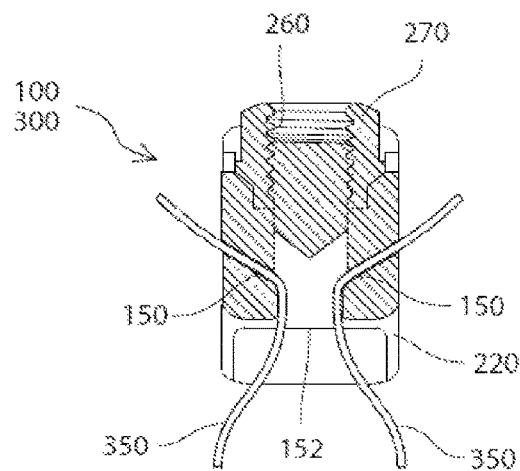
FIG. 27. A cross-sectional front view of an embodiment of connector showing bands in the band channels.
Figure 28:
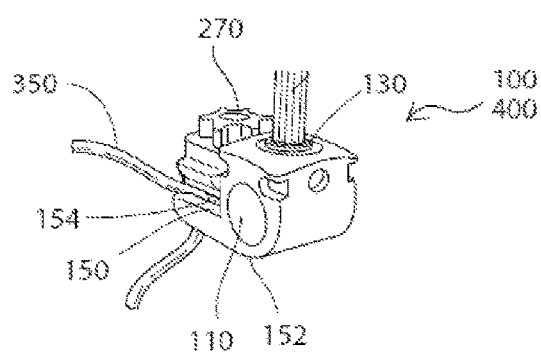
FIG. 28. A perspective view of the embodiment of the connector as shown in FIG. 8 showing bands in the band channels.
Figure 29:
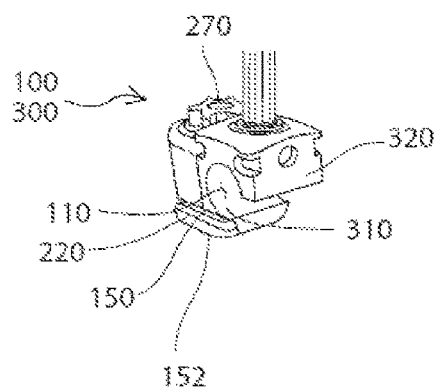
FIG. 29. A perspective view of the embodiment of the connector as shown in FIG. 9 showing bands in the band channels.
Figure 30:
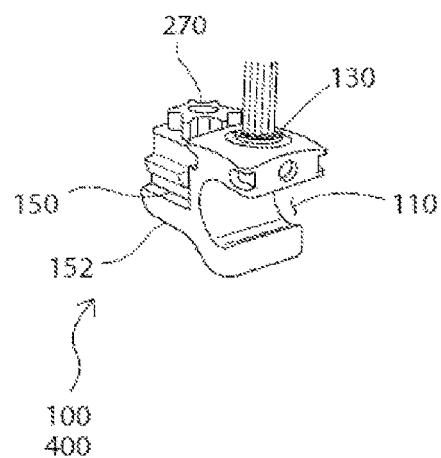
FIG. 30. A perspective view of the embodiment of the connector as shown in FIG. 1 with bands in the band channels.

A specific example of a connector engagement feature 530 is shown in FIGS. 16-21. A clamp locking mechanism is present. The clamp locking mechanism in this embodiment includes an internal ramp structure on an internal surface of the distal end 510 of the instrument 500 that decreases in width in the proximal direction. As can be best seen in FIGS. 25-26, the outermost housing 508 of the reduction instrument 500 has an internal contour that widens in the distal direction and narrows in the proximal direction. This takes the form of a "ramp" between a wider region at the distal end 510 and a narrower region just proximal to the ramp. The clamp locking mechanism shown also comprises a boot member 600 that translates longitudinally relative to the outer housing 508. The boot has an internal side 620 and an external side 640, and is dimensioned to internally accept the proximal end 104 of the connector 100. The boot member 600 also has a plurality of detent members 610 (balls as shown in the figures) each in a cavity that allows the detent member 610 to translate radially from the outer side 640 of the boot member 600 to the inner side 620 of the boot member 600. The detent members 610 are positioned in the cavities such that they translate longitudinally with the boot member 600. FIG. 25 shows the locking mechanism in its unlocked configuration, in which the boot member 600 is positioned so that the detent members 610 contact the distal, broader part of the ramp formation. FIG. 26 shows the locking mechanism in its locked configuration, in which the boot member 600 is positioned so that the detent members 610 contact the narrower proximal portion of the ramp formation 80, which causes the detent members 610 to translate inward radially. This allows the detent members 610 to engage depressions in the proximal end 104 of a connector 100 when the connector 100 is pressed against the boot member 600. The boot member 600 can be translated longitudinally by any suitable mechanism. For example, the boot 600 may be coupled to a thumb wheel 750 on a spiral track, such that rotation of the thumb wheel 750 causes translation of the thumb wheel 750 and the boot longitudinally.

The band slots 550 on the band connection ring 584 will be positioned to provide balanced tension to the bands. In a specific embodiment of the instrument 500, the band slots 550 are positioned approximately 180° from one another on the band connection ring 584. Such an instrument 500 has the advantage of providing high stability when the band 350 is under high tension.

The band connection ring 584 and the band locking ring 552 work together to allow tension on the band to be maintained without constant human intervention. Some previous approaches require that a user maintain tension manually while band tension is locked on the connector 100. The inventive instrument 500 provides a locking mechanism on the instrument 500 itself that it simple for the operator to use and does not require manual strength. When the band slots 550 are aligned with the indentations 590, there is no obstruction to pulling the bands through the slots (or loosening them through the slots). As a result the bands can be pulled to increase tension while the band slots 550 are aligned with the indentation. The configuration in which the indentations 590 are aligned with the band slots 550 is shown in FIG. 22. Once sufficient tension has been achieved, the band locking ring 552 is rotated so that the indentations 590 are no longer aligned with the band slots 550; this wedges the band between the band locking ring 552 and the top of the band slot 550. Some embodiments of the band connection ring 584 comprise gripping or high-friction elements at the exit 154 of the band channel 150, such as the teeth shown in FIGS. 22 and 23. The configuration in which the indentations 590 are not aligned with the band slots 550 is shown in FIG. 23.

Once the band 350 is locked into place relative to the instrument 500, tension is placed on the band 350 by translating the band holder 540 in the proximal direction. An example of the translation mechanism can be seen in FIG. 20. In that illustrated embodiment the band holder translation mechanism comprises a threaded shaft 710 that is free to rotate relative to the band holder 540, and a threaded surface 720 on the band holder 540 engaged to the threaded shaft 710, such that rotation of the threaded shaft 710 results in longitudinal translation of the band holder 540. The threaded shaft 710 is rotated using a knob 740 on the proximal end of the device. The threaded surface 720 on the band holder 540 is a threaded plate on the interior surface of the band holder 540 that is engaged to the threaded shaft 710, and attached to the band holder 540 such that the threaded plate and the band holder 540 translate together longitudinally. As can be seen in FIG. 20, the threaded shaft 710 in the illustrated embodiment comprises external threads and is positioned to the interior of the band holder 540.

A method is provided for anchoring a spinal rod to a bone structure using the systems described above. A general embodiment of the method comprises: positioning a flexible band around the bone structure to make contact between a middle portion of the band and said bone structure; connecting a pair of terminal portions of the flexible band to a connector 100, the connector 100 comprising a pair of band channels 150 and the spinal rod housing 170, wherein each of the pair of terminal portions is in a respective band channel 150; increasing tension on the flexible band in an amount sufficient to cause contact between the connector 100 and the bone structure and sufficient to restrict movement of the connector 100 relative to the bone structure; locking each of the terminal portions of the flexible band the connector 100 by narrowing each of the band channels 150 to prevent release of the tension; and immobilizing the spinal rod in the spinal rod housing 170 to prevent movement of the connector 100 relative to the spinal rod. The connector 100 may be, without limitation, any embodiment of the connector 100 described above.

The flexible band 350 is of suitable construction for implantation in vivo. It is constructed from biocompatible materials, such as woven polyethylene terephthalate fiber. The band is elongate in shape, having a middle section and two terminal sections. In use the middle section is looped or wrapped around the bone structure, and the terminal sections are threaded through the band channels 150 of the connector 100.

Tension is increased on the band to produce the desired degree of restriction of motion between the connector 100 and the bone. The tension may be produced by pulling the terminal sections away from the connector 100, either manually or using a tensioning instrument 500. For example, the tension may be produced using any embodiment of the tensioning instrument 500 described above.

The terminal portions of the band are "locked" to the connector 100 such that the tension on the band between the connector 100 and the bone structure is maintained indefinitely. Each terminal portion of the band is locked into a separate band channel 150. In embodiments in which the two terminal portions share portions of their respective band channels 150, locking occurs in portions of the channels that are separate from one another. This has the advantage of preventing interference between the two terminal portions of the band from compromising the locking force (i.e., friction) on one or both of the band portions.

The rod can be immobilized by any suitable means. For example, the rod may be immobilized in the connector 100 using a locking cap 130 arrangement as described above for the dual-lock embodiments 400 of the connector 100; or alternatively the rod may be immobilized in the connector 100 using a rod channel 110 with two sections (e.g., an upper housing section 220 and a lower housing section 310) as described above for the single-lock embodiments 300 of the band channel 150.

Some embodiments of the method have the advantage of allowing the tension to be increased on the band 350 without affecting the tension or compression exerted by the band or the connector 100 on the spinal rod. Unlike some prior approaches, the current method may be designed to allow the band tensioning step to be distinct from the rod immobilizing step. This has the advantage of allowing the rod to be inserted, adjusted, and immobilized relative to the connector 100 after the connector 100 has been secured to the bone using the band. In some further embodiments, the band 350 does not contact the rod channel 110 when the band 350 is connected to the connector 100, for example, as illustrated in a non-limiting example of FIG. 3A.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

In an alternative method, the connector 100 may be attached to a rod near the proximal end of a fixation construct. The band may be wrapped around (or, through a hole formed therein) one or more of a lamina(s), transverse process(s), spinous process(s), and rib(s) of one or more vertebrae proximal to the end of the construct and then tensioned and locked to the connector 100 as previously described. This configuration may provide additionally stability to the spine adjacent the construct while reducing the forces that may help contribute to adjacent segment disease.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A device for tensioning a band connected to a connector, the device comprising:
    an elongate shaft having a distal end and a proximal end;
    an engagement feature at the distal end of the elongate shaft, the engagement feature configured to engage the connector; and
    a band holder comprising a band connection ring having two band slots configured to receive the band and a band locking ring having two indentations, wherein, in a first configuration of the band holder, each of the two indentations is aligned with a respective one of the two band slots to allow the band to pass through one of the two band slots, and in a second configuration of the band holder, each of the two indentations is rotated relative to the respective one of the two band slots to restrict movement of the band.

2. The device of claim 1, wherein the elongate shaft comprises a threaded surface, and the band holder comprises an engaging threaded surface such that rotation of the elongate shaft causes longitudinal translation of the band holder.

3. The device of claim 1, wherein the two band slots are positioned opposite each other on the band connection ring.

4. The device of claim 1, wherein the band is positioned around a bone structure and reversibly connected to the connector.

5. The device of claim 1, wherein the engagement feature comprises a clamp locking element, and wherein the clamp locking element includes a ramped contour that has an increased width at a distal end of the clamp locking element relative to a width at a proximal end of the clamp locking element.

6. The device of claim 5, wherein the clamp locking element comprises a boot element configured to translate longitudinally relative to the elongate shaft.

7. The device of claim 6, wherein the boot element comprises one or more cavities, each of the one or more cavities holding a detent member configured to translate radially relative to the ramped contour.

8. The device of claim 7, wherein the engagement feature is configured to be in a locked configuration in which the detent member contacts a proximal end of the ramped contour, or in an unlocked configuration in which the detent member contacts a distal end of the ramped contour.

9. The device of claim 7, wherein the detent member is configured to translate radially inward and engage a proximal end of the connector.

10. The device of claim 6, further comprising a thumb wheel configured to rotate, thereby causing translation of the boot element longitudinally, and switching the engagement feature between a locked configuration and an unlocked configuration.

11. A device for tensioning a band connected to a connector, the device comprising:
    an elongate shaft having a distal end and a proximal end;
    an engagement feature at the distal end of the elongate shaft, the engagement feature configured to engage the connector; and
    a band holder comprising a band connection ring having two band slots configured to receive the band and a band locking ring having two indentations, wherein, when the band locking ring is rotated such that the two indentations are not aligned with the two band slots, longitudinal translation of the band relative to the band holder is restricted or prevented.

12. The device of claim 11, wherein the elongate shaft comprises a threaded surface, and the band holder comprises an engaging threaded surface such that rotation of the elongate shaft causes longitudinal translation of the band holder.

13. The device of claim 11, wherein the two band slots are positioned opposite each other on the band connection ring.

14. The device of claim 11, wherein the band is positioned around a bone structure and reversibly connected to the connector.

15. The device of claim 11, wherein the engagement feature comprises a clamp locking element, and wherein the clamp locking element includes a ramped contour that has an increased width at a distal end of the clamp locking element relative to a width at a proximal end of the clamp locking element.

16. The device of claim 15, wherein the clamp locking element comprises a boot element configured to translate longitudinally relative to the elongate shaft.

17. The device of claim 16, wherein the boot element comprises one or more cavities, each of the one or more cavities holding a detent member configured to translate radially relative to the ramped contour.

18. The device of claim 17, wherein the engagement feature is configured to move between a locked configuration in which the detent member contacts a proximal end of the ramped contour, and an unlocked configuration in which the detent member contacts a distal end of the ramped contour.

19. The device of claim 17, wherein the detent member is configured to translate radially inward and engage a proximal end of the connector.

20. The device of claim 16, further comprising a thumb wheel configured to rotate, thereby causing translation of the boot element longitudinally and switching the engagement feature between a locked configuration and an unlocked configuration.

* * * * *